United States Patent
Vohwinkel et al.

(10) Patent No.: US 11,058,591 B2
(45) Date of Patent: *Jul. 13, 2021

(54) FEMININE HYGIENE ARTICLE WITH IMPROVED WINGS

(71) Applicant: The Procter & Gamble Company, Cincinnati, OH (US)

(72) Inventors: Henning Vohwinkel, Kronberg (DE); Wolfgang Domeier, Frankfurt Am Main (DE); Rainer Hefele, Wurzburg (DE); Bruce William Lavash, West Chester, OH (US); Holger Wendt, Schwalbach am Taunus (DE)

(73) Assignee: The Procter & Gamble Company, Cincinnati, OH (US)

(*) Notice: Subject to any disclaimer, the term of this patent is extended or adjusted under 35 U.S.C. 154(b) by 420 days.

This patent is subject to a terminal disclaimer.

(21) Appl. No.: 15/977,047

(22) Filed: May 11, 2018

(65) Prior Publication Data

US 2018/0325751 A1 Nov. 15, 2018

Related U.S. Application Data

(60) Provisional application No. 62/505,154, filed on May 12, 2017.

(51) Int. Cl.
*A61F 13/84* (2006.01)
*A61F 13/56* (2006.01)
(Continued)

(52) U.S. Cl.
CPC ........ *A61F 13/5616* (2013.01); *A61F 13/472* (2013.01); *A61F 13/476* (2013.01);
(Continued)

(58) Field of Classification Search
USPC .................................................. 604/385.04
See application file for complete search history.

(56) References Cited

U.S. PATENT DOCUMENTS

| | | | | |
|---|---|---|---|---|
| 5,401,268 A | * | 3/1995 | Rodier | A61F 13/15577 604/385.04 |
| 6,689,112 B1 | * | 2/2004 | Blanchard | A61F 13/476 604/385.04 |

(Continued)

FOREIGN PATENT DOCUMENTS

| | | |
|---|---|---|
| AR | 92853-0001 | 3/2018 |
| EP | 1208823 A1 | 5/2002 |

(Continued)

OTHER PUBLICATIONS

U.S. Appl. No. 15/976,901, filed May 11, 2018, Vohwinkel et al.

(Continued)

*Primary Examiner* — Michele M Kidwell
(74) *Attorney, Agent, or Firm* — George H. Leal

(57) ABSTRACT

Feminine hygiene articles are disclosed herein. The feminine hygiene articles described herein can provide easily discernable placement and orientation guides which reduce the likelihood of misapplication by the user, facilitated attachment guides which can reduce the likelihood of misapplication of the feminine pad and can also reduce the likelihood of improper attachment of the feminine pad to a panty. The feminine hygiene articles disclosed include uniquely shaped wings which can provide cues on proper attachment of the article to the panty, and may help in providing sustained coverage of the feminine hygiene article to the panty which reduces the likelihood that the pad will become detached during use.

20 Claims, 27 Drawing Sheets

(51) Int. Cl.
*A61F 13/472* (2006.01)
*A61F 13/476* (2006.01)
*A61F 13/15* (2006.01)

(52) U.S. Cl.
CPC ........ *A61F 13/47245* (2013.01); *A61F 13/84* (2013.01); *A61F 13/15723* (2013.01); *A61F 2013/8497* (2013.01)

(56) References Cited

U.S. PATENT DOCUMENTS

| | | | |
|---|---|---|---|
| 8,986,273 B2 | 3/2015 | Mercer et al. | |
| 2002/0165512 A1* | 11/2002 | Drevik | A61F 13/47245 604/380 |
| 2004/0138636 A1 | 7/2004 | Cardin et al. | |
| 2004/0243087 A1 | 12/2004 | Kinoshita et al. | |
| 2005/0124959 A1 | 6/2005 | Alcantara et al. | |
| 2005/0261652 A1* | 11/2005 | Digiacomantonio | A61F 13/84 604/385.03 |
| 2005/0283131 A1 | 12/2005 | Zander et al. | |
| 2006/0116652 A1 | 6/2006 | Miura et al. | |
| 2006/0142710 A1* | 6/2006 | Kigata | A61F 13/4751 604/361 |
| 2007/0100309 A1* | 5/2007 | Uda | A61F 13/476 604/385.04 |
| 2008/0015536 A1* | 1/2008 | Digiacomantonio | A61F 13/5616 604/385.04 |
| 2013/0123731 A1* | 5/2013 | Mercer | A61F 13/5616 604/385.04 |
| 2014/0288520 A1* | 9/2014 | Kuramochi | A61F 13/5616 604/385.04 |
| 2014/0343525 A1* | 11/2014 | Roh | A61F 13/4751 604/385.04 |
| 2015/0057632 A1 | 2/2015 | Luzader et al. | |
| 2016/0235607 A1 | 8/2016 | Mercer et al. | |
| 2016/0331598 A1* | 11/2016 | Morrison | A61F 13/51394 |
| 2017/0354549 A1* | 12/2017 | Cho | A61F 13/472 |
| 2018/0325750 A1* | 11/2018 | Vohwinkel | A61F 13/47245 |
| 2018/0325751 A1* | 11/2018 | Vohwinkel | A61F 13/472 |
| 2018/0325754 A1* | 11/2018 | Vohwinkel | A61F 13/472 |
| 2019/0290506 A1* | 9/2019 | Kuramochi | A61F 13/513 |

FOREIGN PATENT DOCUMENTS

| | | | | |
|---|---|---|---|---|
| EP | 1293186 | * | 3/2003 | ........... A61F 13/475 |
| EP | 2216003 A1 | | 8/2010 | |
| EP | 3075365 A1 | | 10/2016 | |
| EP | 3505148 | * | 7/2019 | ........... A61F 13/472 |
| JP | 2003339764 A | | 12/2003 | |
| JP | 2013009892 A | | 1/2013 | |
| JP | 2013220225 A | | 10/2013 | |
| JP | 2014-223216 | * | 12/2014 | ............. A61F 13/15 |
| WO | WO2010110270 A1 | | 9/2010 | |
| WO | 2019/008090 | * | 1/2019 | ........... A61F 13/472 |

OTHER PUBLICATIONS

U.S. Appl. No. 15/976,946, filed May 11, 2018, Vohwinkel et al.
U.S. Appl. No. 15/977,025, filed May 11, 2018, Vohwinkel et al.
Search Report and Written Opinion for PCT/US2018/032309 dated Jul. 31, 2018.
International Search Report and Written Opinion for PCT/US2018/032320 dated Jul. 31, 2018.
International Search Report and Written Opinion for PCT/US2018/032322 dated Aug. 6, 2018.
International Search Report and Written Opinion for PCT/US2018/032323 dated Aug. 6, 2018.
All Office Actions for U.S. Appl. No. 15/976,901, filed May 11, 2018.
All Office Actions for U.S. Appl. No. 15/976,946, filed May 11, 2018.
All Office Actions for U.S. Appl. No. 15/977,025, filed May 11, 2018.

* cited by examiner

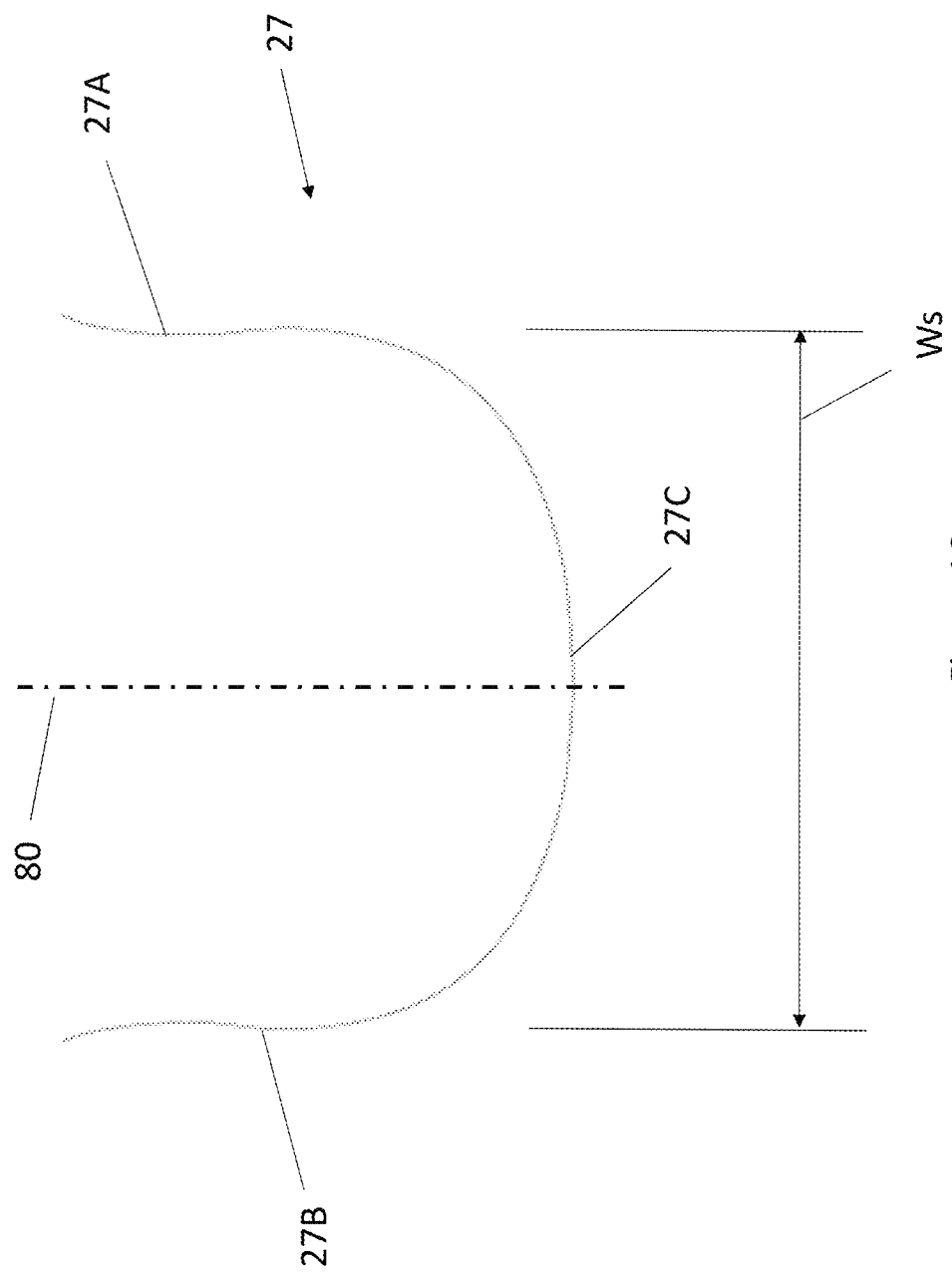

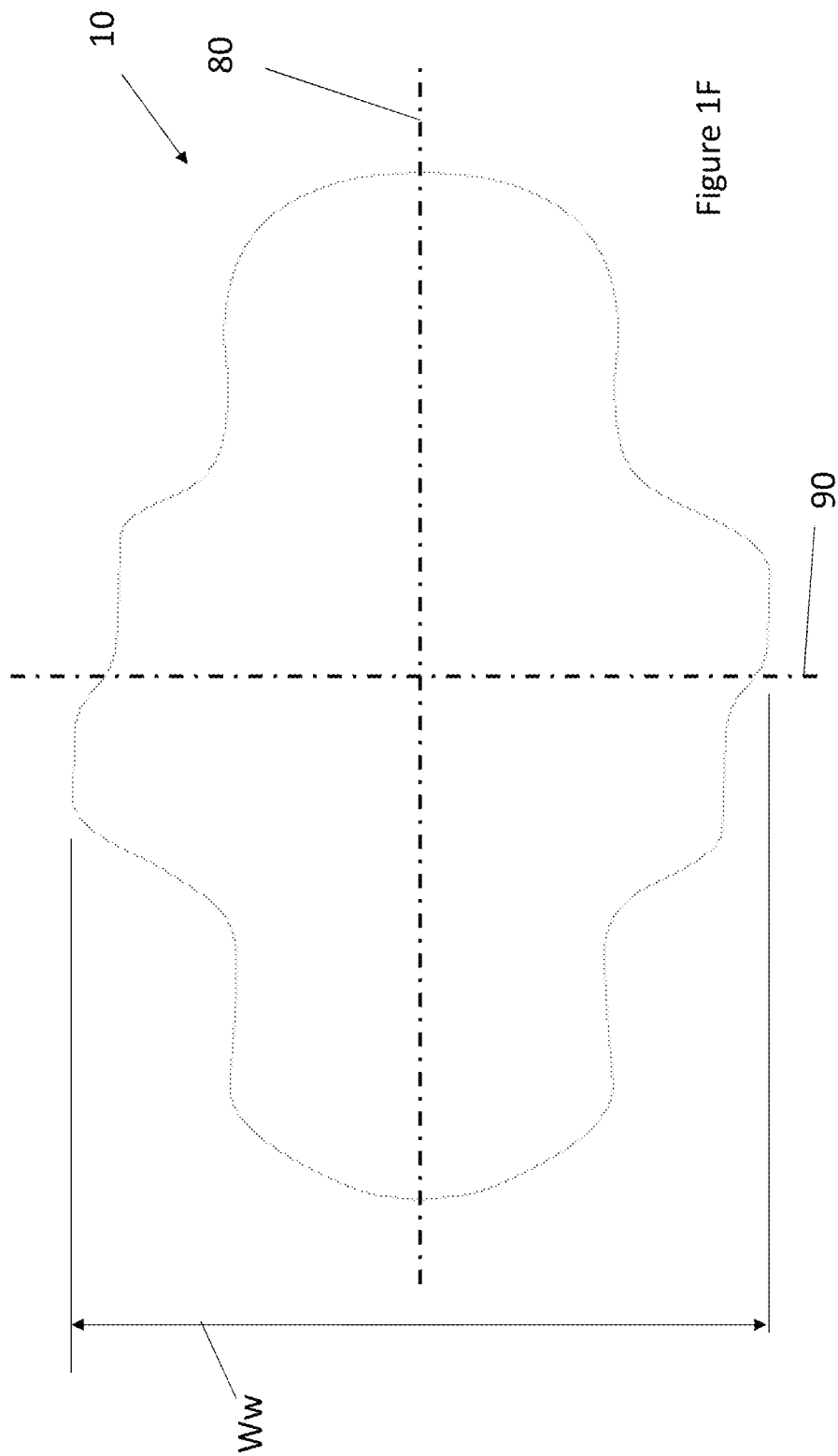

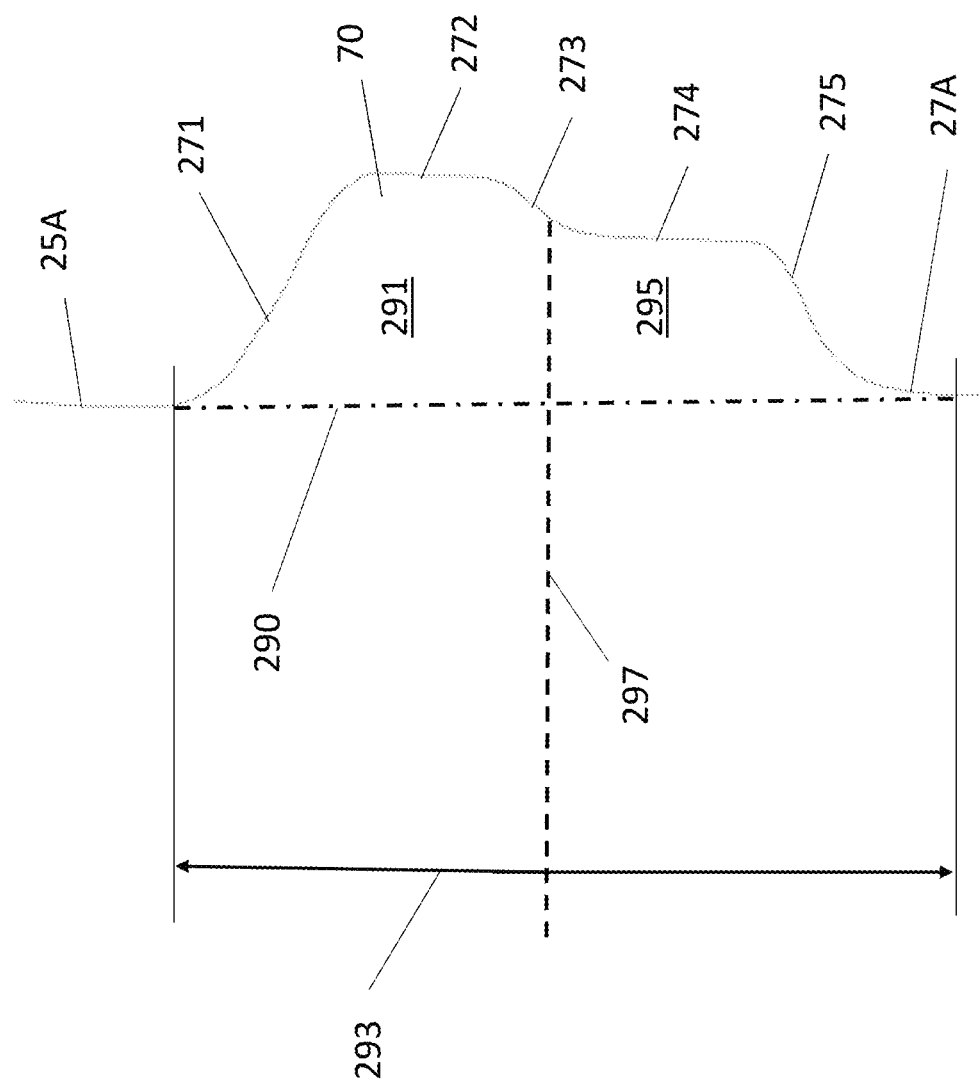

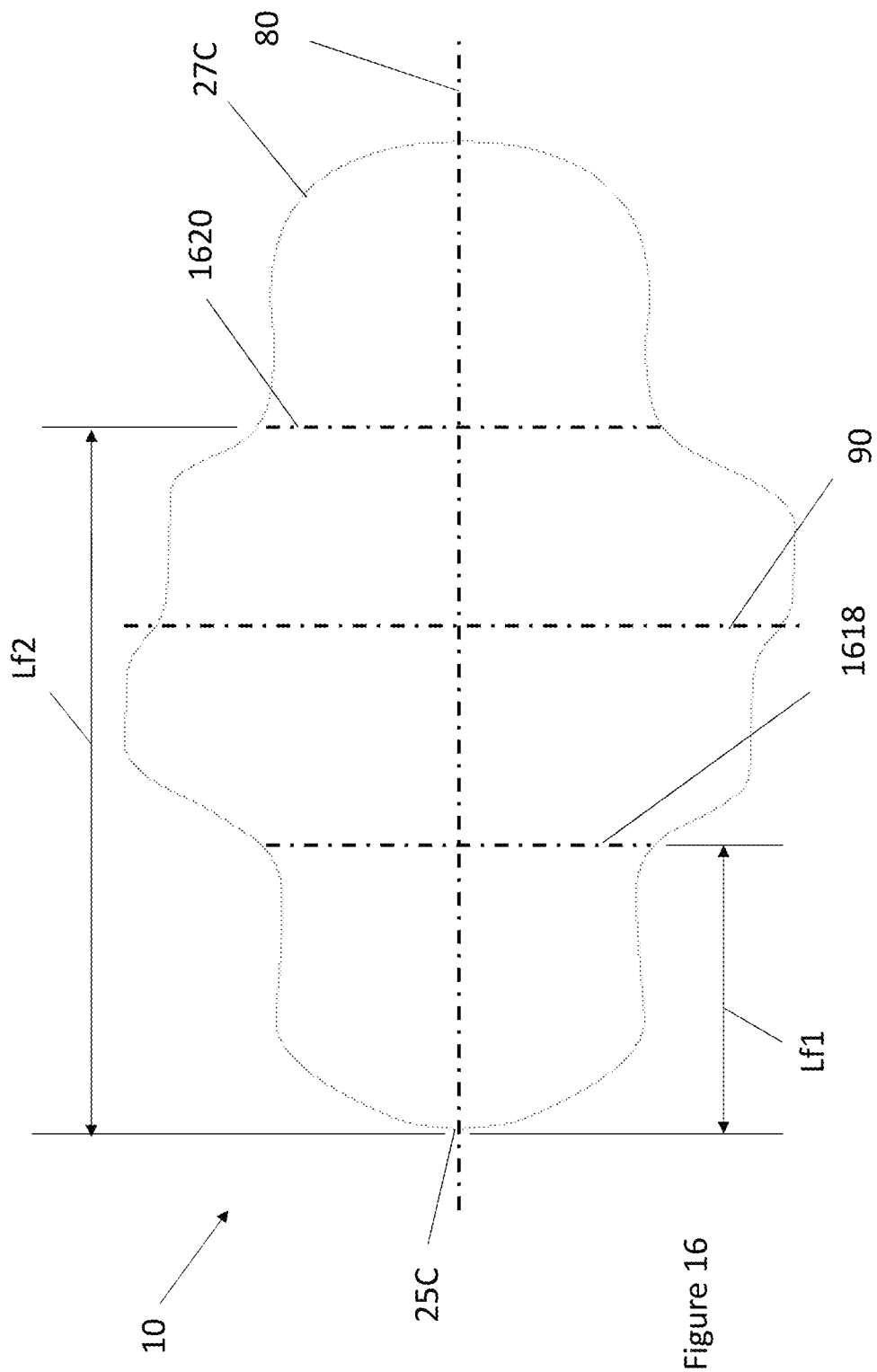

US 11,058,591 B2

FEMININE HYGIENE ARTICLE WITH IMPROVED WINGS

FIELD OF THE INVENTION

The present application pertains to absorbent articles and more particularly to feminine hygiene articles.

BACKGROUND OF THE INVENTION

Feminine pads have been used widely for several decades. These pads are generally utilized during menstruation to capture menses and wetness. In general, the user of feminine pads wants to feel clean and dry. Many advancements in feminine pad technology have attempted to improve one or both of these aspects. For example, wings were introduced to the feminine pads to reduce the likelihood of leakage and to help secure the pad to the panty of the wearer. Additionally, absorbent core materials have been introduced which can provide enhanced absorbent capacity in a relatively thin pad.

However, providing the user of feminine pads the desired experience is a bit more complex and requires more than the above advancements. The user of the feminine pad should be provided with an easy to discern application guide which ensures the proper placement/orientation of the feminine pad within the panty. If improper placement and/or orientation is utilized, the above advancements of wings and absorbent core materials will likely not provide the intended benefit. Additionally, the pad must be securely fastened to the panty. Without the secure fastening of the feminine pad to the panty, the feminine pad may become detached during use. And similar to improper placement and/or orientation, detachment can negate much of the functionality of the advancements described above.

Secure attachment of the feminine pad to the panty can generally include two aspects. First, proper attachment of the pad to the panty, and second, sustained attachment/coverage of the feminine pad to the panty. Unfortunately, without proper attachment, sustained attachment and coverage may be difficult to achieve. And, in some instances, proper attachment does not necessarily guarantee sustained attachment/coverage.

Based on the foregoing, it would be beneficial to provide a pad which provided easily discernable placement/orientation guides, facilitated attachment guides, and/or sustained attachment to the panty.

SUMMARY OF THE INVENTION

The feminine hygiene article of the present invention can provide the user with an intuitive application guide which facilitates the identification of proper orientation of the pad. In some forms, the feminine hygiene article of the present invention can provide the user with an intuitive application guide which facilitates proper application of the pad to a panty. And, in some forms, the feminine hygiene article of the present invention can provide sustained coverage of the feminine hygiene article to the panty.

In some forms, a feminine hygiene article has a chassis comprising a topsheet, a backsheet, and an absorbent core disposed between the topsheet and the backsheet. The feminine hygiene article further comprises a longitudinal centerline and a lateral centerline perpendicular to the longitudinal centerline; a first end, an opposing second end, and an intermediate region connecting the first end and the second end, the first end having a width Wf and the second end having a width Ws.

The feminine hygiene article further comprises a first wing extending laterally outboard of the chassis having a first leading edge extending outboard of the chassis, a first trailing edge extending outboard of the chassis and one or more edges connecting the first leading edge and the first trailing edge, wherein the first wing has a first length and a first bisecting line bisecting the first length, the first bisecting line forming, at least a portion, of a boundary between a first distal zone and a first proximal zone, wherein the first wing is asymmetric about the first bisecting line, wherein the first wing further comprises a first surface (501) and an opposing second surface, a first adhesive area and a second adhesive area disposed on the second surface, wherein the first adhesive area is disposed asymmetrically with respect to the first bisecting line.

The feminine hygiene article further comprises a second wing extending laterally outboard of the chassis having a second leading edge extending outboard of the chassis, a second trailing edge extending outboard of the chassis and one or more edges connecting the second leading edge and the second trailing edge, wherein the second wing has a second length and a second bisecting line bisecting the second length, wherein the second wing is asymmetric about the second bisecting line, wherein the second wing further comprises a first surface and an opposing second surface, a third adhesive area and a fourth adhesive area disposed on the second surface, wherein the third adhesive area is disposed asymmetrically with respect to the second bisecting line. A first visual signal is disposed on the first wing, wherein the first visual signal comprises a first visual signal area, and wherein the first visual signal area is disposed asymmetrically with respect to the first bisecting line as determined by the Visual Signal Area Measurement Method disclosed herein. And, a second visual signal is disposed on the second wing, wherein the second visual signal comprises a second visual signal area, and wherein the second visual signal area is disposed asymmetrically with respect to the second bisecting line as determined by the Visual Signal Area Measurement Method disclosed herein.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings described below.

FIG. 1C is an illustration of a second end of the feminine pad of FIG. 1A.

FIG. 1F is an illustration of the feminine pad of FIG. 1A highlighting the width thereof.

FIG. 2B is an illustration of a second wing of the feminine pad of FIG. 1A.

FIG. 16 is a representation showing a feminine pad constructed in accordance with the present disclosure.

DETAILED DESCRIPTION OF THE INVENTION

Figure 1A:
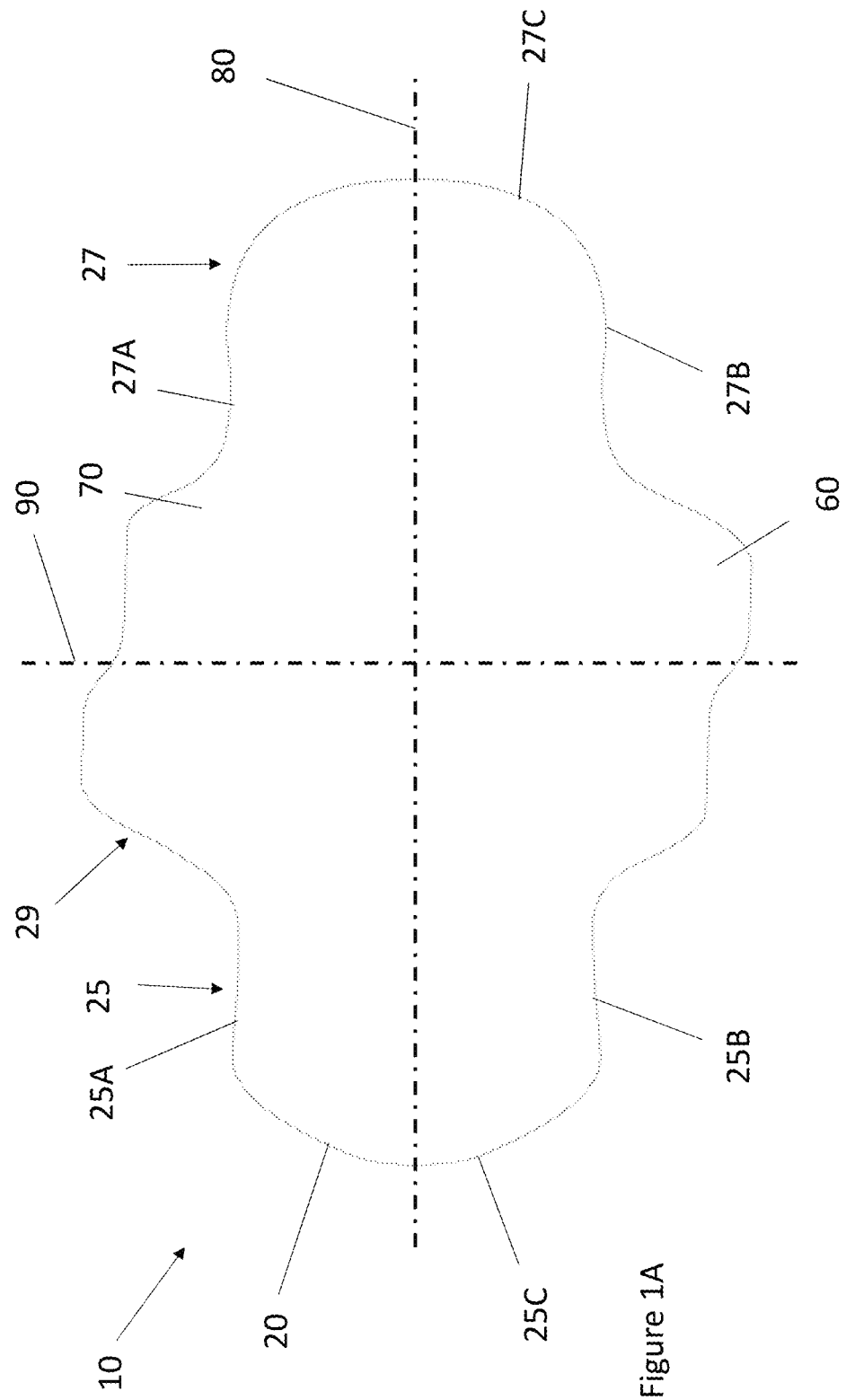
FIG. 1A is a representation of a feminine pad in accordance with the present disclosure.

The feminine pad according to the present disclosure can provide easily discernable placement and orientation guides which reduce the likelihood of misapplication by the user. The feminine pad of the present disclosure has a unique shape, including a pair of wings which are uniquely shaped, collectively which act as an easily discernable placement/orientation guide for a user. The easily discernable placement/orientation guide reduces the likelihood of misapplication of the feminine pad, and therefore increasing the likelihood of a good user experience. Additionally, these placement/orientation guides can be provided in an array of products which similarly may facilitate the use of variable sized articles within the array. Each of these features is discussed in additional detail herein.

As used herein "array" means a display of packages comprising disposable articles of different sizes having like article constructions (e.g., same elastomeric materials [compositionally and/or structurally] in the flaps, graphic elements) said packages having the same brand and/or sub-brand, and said packages oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Depend," and same sub-brand, for example, "for Women Underwear." A different array may have the brand "Depend" and the sub-brand "Silhouette For Women." The differences between the "for Women Underwear" array and the "Silhouette For Women" arrays include different elastomeric materials in the side flaps, where "for Women Underwear" comprises strands as the elastomeric material and "Silhouette For Women" comprises a film elastomeric material." Furthermore, the packaging is distinctly different in that "for Women Underwear" is packaged in a predominately green, film bag and "Silhouette For Women" is packaged in a predominately maroon box. Further regarding "Arrays," as another example of two separate "arrays" having the same brand, "Certainty," one line-up has the sub-brand "Women's Underwear." A different array may have the same brand "Certainty" and the sub-brand "Smooth Shape Briefs for Women." The differences between the "Women's Underwear" array and the "Smooth Shape Briefs for Women" arrays include different elastomeric materials in the side flaps, where "Women's Underwear" comprises strands as the elastomeric material and "Smooth Shape Briefs for Women" comprises a film elastomeric material." Furthermore, the packaging is distinctly different in that "Women's Underwear" is packaged in a predominately blue, film bag and "Smooth Shape Briefs for Women" is packaged in a predominately maroon box.

Arrays also often have the same trademarks, including trademarks of the brand, sub-brand, and/or features and/or benefits across the line-up.

"On-line Array" means an "Array" distributed by a common on-line source.

It will be appreciated that pads of the present disclosure may take a multitude of different forms while still providing intuitive pad orientation and attachment cues to a user which in turn provide optimized and sustained coverage when the pad is attached to a panty. Pads of the present disclosure comprise a first end, a second end opposing the first end, and an intermediate region joining the first end and the second end. In some forms, a width $W_f$ of the first end is less than a width $W_s$ of the second end. Having a narrower first end helps a user to intuitively know which way the pad should be oriented when in use.

Furthermore, pads of the present disclosure have first and second wings, extending laterally outboard of the chassis in opposing directions, generally in the area of the intermediate region. First and second wings are asymmetric about bisecting lines that are coincident with or substantially parallel to a lateral centerline of the pads. The asymmetric wings enable the pads to be securely fastened to a user's underwear when in use by providing cues for the user on how and where to fasten the wings on an underside of the underwear.

In pads of the present disclosure, the first wing is divided into first distal and first proximal zones, and the second wing is divided into second distal and second proximal zones. The first and second distal zones comprise an edge of each respective wing that is located furthest outboard of the chassis. That is, the first distal zone comprises an edge of the first wing located furthest outboard of the chassis and, by contrast, an edge of the first proximal zone is located nearer the chassis. Similarly, the second distal zone comprises an edge of the second wing located furthest outboard of the chassis and the second proximal zone comprises an edge that is located nearer the chassis. The presence of a distal zone that extends from the chassis beyond the proximal zone of the wing provides a clear indication to a user where they should grab the wing when fastening to a panty.

In some forms, the first distal zone and second distal zone are longitudinally offset from each other. For example, if the first distal zone is located proximal to the first end of the pad, the second distal zone is located proximal to the second end of the pad. Where the distal zones of the first and second wings are longitudinally offset from each other, the wings may be securely fastened on the underside of a panty without overlapping.

Each of these areas can play a role in providing intuitive pad orientation cues which in turn can provide intuitive pad attachment cues. Each of the first end, second end, and intermediate regions are discussed in additional detail herein. And, while the description herein references "feminine pads" or "feminine hygiene pads," the features of the article described herein shall be equally applicable to panty liners, menstrual pads, and adult incontinence pads.

Pad Orientation/Placement

FIGS. 1 to 16 describe different examples of absorbent articles—or components thereof—of the present disclosure that may share the features described above. A feminine hygiene pad constructed in accordance with the present disclosure is shown in FIG. 1A. FIG. 1A depicts an outer periphery of a feminine pad 10. The feminine pad 10 may comprise a chassis 20 and a pair of wings 60 and 70 extending outboard of the chassis 20. The chassis 20 has a first end 25 and a second end 27 and an intermediate region 29 disposed between the first end 25 and the second end 27. The feminine pad 10 further comprises a longitudinal centerline 80 and a lateral centerline 90 which is disposed generally perpendicular to the longitudinal centerline 80. And, the chassis 20 may further comprise a topsheet, a backsheet, and an absorbent core disposed between the topsheet and the backsheet. The topsheet, backsheet, and absorbent core are discussed in additional detail herein.

Regarding the chassis 20, the first end 25 comprises a pair of longitudinal side edges 25A and 25B and a first end edge 25C which joins the longitudinal side edges 25A and 25B. The longitudinal side edges 25A and 25B may be disposed generally parallel to the longitudinal centerline 80. Similarly, the second end 27 may comprise a pair of longitudinal side edges 27A and 27B which are disposed generally parallel to the longitudinal centerline 80. A second end edge 27C joins the longitudinal side edges 27A and 27B. Note that the term "generally parallel" does not require the longitudinal side edges to be absolutely parallel. In the specific case of the longitudinal side edges 25A, 25B, 27A and 27B, their respective inclination to the longitudinal centerline 80 is discussed in additional detail herein.

The delineation between the first end 25, second end 27, and intermediate region 29 can be dependent upon the extension of the wings from the chassis 20. For example, the delineation between the first end 25 and the intermediate region 29 can be approximated by determining a first intersection point between longitudinal side edge 25A and a leading edge of wing 70 and a second intersection point between longitudinal side edge 25B and a leading edge of wing 60. A first line generally parallel to the lateral centerline 90 extending from the first intersection point to the second intersection point, provides a useful approximation of the delineation between the first end 25 and the intermediate region 29. As another example, the delineation between the second end 27 and the intermediate region 29 can be determined in much the same way as described above. For example, finding a third intersection point between a trailing edge of wing 70 and the longitudinal side edge 27A and a fourth intersection point between a trailing edge of wing 60 and the longitudinal side edge 27B can be helpful. A second line generally parallel to the lateral centerline 90 extending from the third intersection point to the fourth intersection point, provides a useful approximation of the delineation between the second end 27 and the intermediate region 29. The pertinent edges of the wings 60 and 70 are discussed in additional detail hereafter.

Figure 1B:
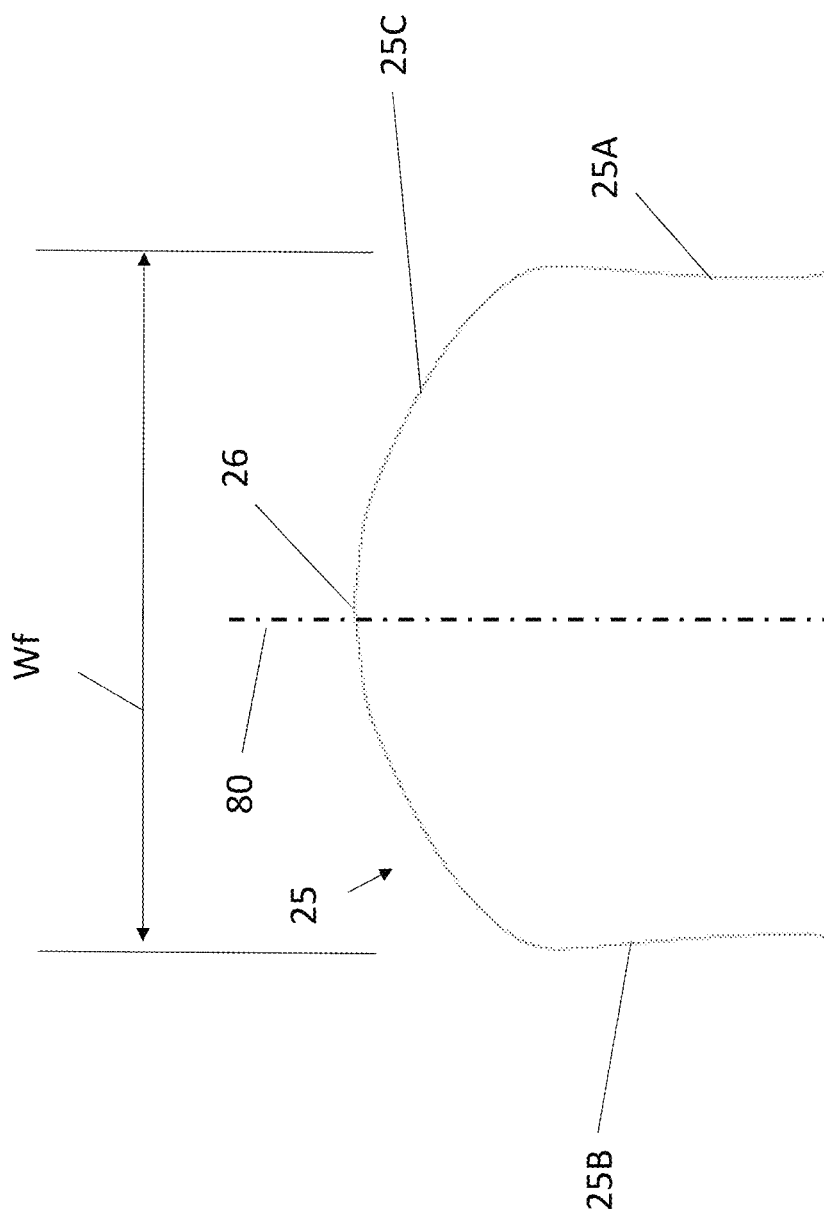
FIG. 1B is an illustration of a first end of the feminine pad of FIG. 1A.

Focusing on the first end 25 in FIG. 1B, it is worth noting that the first end edge 25C tapers toward an apex 26. The tapering of the first end edge 25C toward the apex 26 in the first end 25 can help a wearer identify the correct orientation of the feminine pad 10 in the panty. For example, due to the tapering of the first end edge 25C toward the apex 26, a user may be able to more easily identify a front of the feminine pad 10 as opposed to the second end edge 27C which is more rounded as discussed below.

As shown, the first end 25 may also comprise a width Wf which is generally parallel to the lateral centerline 90 (shown in FIG. 1A). The width Wf represents the widest portion of the first end 25. The width Wf is discussed in additional detail hereafter.

Additionally, the first end edges 25A and 25B may be inclined slightly inward from the first end edge 25C. Such inclination by the first end edges 25A and 25B provide for a smaller width chassis 20 moving from the first end 25 toward the intermediate region 29. This inclination by the first end edges 25A and 25B may generally follow the contour of the panty thereby providing a more comfortable fit within the panty of the wearer.

Moreover, inclined first end edges 25A and 25B can increase the longevity of a rotary knife system. Rotary knife systems typically comprise a die cutting roll and an anvil roll and may be utilized to cut the final shape of the pad from their respective webs. Edges which are generally parallel to an MD direction (generally parallel to the longitudinal centerline 80) can prematurely wear the anvil roll. In such instances, blades of the die cutting roll strike the anvil roll in generally a small band width in a CD direction (generally parallel to the lateral centerline 90). Such repeated strikes can prematurely wear the die cutting roll and/or the anvil roll. However, where edges are inclined, such as first end edges 25A and 25B, blades of the die cutting roll strike the anvil roll along an increased band width in the CD direction. The larger band width on the anvil roll can extend the longevity of the anvil roll.

Focusing on the second end 27 in FIG. 1C, the second end edge 27C, unlike the first end edge 25C (shown in FIG. 1B), may be more rounded. Again, because of the difference between the first end edge 25C (shown in FIG. 1B) and the second end edge 27C, the likelihood of misapplication of the feminine pad 10 to the panty may be decreased. For example, because of the shape differences between the first end edge 25C and the second end edge 27C, a user may be more inclined to orient the first end edge 25C in the front of the panty and the second end edge 27C in the back of the panty—which is the appropriate application.

Additionally, the second end 27 may comprise a width Ws which is generally parallel to the lateral centerline 90. The width Ws represents the widest portion of the second end 27 of the feminine pad 10. The width Ws is discussed in additional detail hereafter.

The side edges 27A and 27B of the second end 27 may be inclined inward from the second end edge 27C. Such inclination of the side edges 27A and 27B can provide for a smaller width chassis 20 moving from the second end 27 toward the intermediate region 29. Much like the first side edges 25A and 25B (shown in FIG. 1B), the inclined second side edges 27A and 27B can provide longevity for the rotary knife system and can follow the contour of the panty to provide more comfort.

Referring now to FIGS. 1A-1C, as noted previously, the feminine pad 10 may comprise a first end width Wf and a second end width Ws. The width of the first end Wf may be from about 80 to 103 mm, from about 86 to 102 mm, or from about 88 mm to about 100 mm specifically including any values within these ranges and any ranges created thereby. In one specific form, Wf may be about 88 mm. The width of the second end Ws may be from about 80 mm to about 170 mm, from about 80 mm to about 140 mm, or from about 80 mm to about 120 mm specifically including any values within these ranges and any ranges created thereby. A ratio of Wf to Ws may be from about 0.47 to about 1.0, from about 0.75 to about 0.95, or from about 0.85 to about 0.90 specifically including any values within these ranges and any ranges created thereby. It is worth noting that Ws for longer pads may be wider to provide additional protection for the user. The second end on longer pads typically corresponds to additional panty area. For the longer pads, e.g. overnight pads, the ratio of Wf to Ws may be about 0.7.

Forms are contemplated where an array of absorbent articles constructed in accordance with the present disclosure is provided. In such forms, a first plurality of articles may have a Wf to Ws ratio of about 1.0 while a second plurality of absorbent articles may have a Wf to Ws ratio of less than 1.0. For example, the second plurality of absorbent articles may have a Wf to Ws ratio of about 0.7. In some forms, a third plurality of articles may have a Wf to Ws ratio of about 1.0. Additional forms are contemplated where a fourth plurality of articles have a Wf to Ws ratio of less than 1.0 but greater than 0.7. Typically, a Wf to Ws ratio of 1.0 or less can help the wearer identify which end of the feminine hygiene article is associated with the anterior of the body and which is associated with the posterior. Where the Wf to Ws ratio is 1.0, differences in shape may be utilized to provide the orientation cues. For example, first end may have a more pointed end versus a more rounded end for the second end. Such cues can help the wearer properly orient the feminine hygiene article appropriately within their underwear.

As noted, the width of the first end 25 may decrease toward the intermediate region 29. Similarly, the width of the second end 27 may decrease toward the intermediate region 29. In some forms, the first end width may decrease to about 53 percent of Wf, about 80 percent of Wf, or about 95 percent of Wf specifically including any values within these ranges and any ranges created thereby. In some forms, independent of or inclusive of the decrease of the first end width, the second end width may decrease to 40 percent of Ws, about 85 percent of Ws, or about 98 percent of Ws specifically including any values within these ranges and any ranges created thereby.

Referring back to FIG. 1A, the intermediate region can also contribute to the easily discernable indication of orientation and placement of the feminine pad 10. The intermediate region 29, corresponds to an area of the pad which comprises a target fluid entry zone. Additionally, the intermediate region 29 comprises wings 60 and 70 which extend outboard of the chassis 20. The wings of the present disclosure can help provide a user with a placement guide such that the vaginal opening corresponds to the intermediate region 29 and the target fluid entry zone of the feminine pad.

The target fluid entry zone of the feminine pad 10 should line up with the vaginal opening. And the target fluid entry zone for the feminine pads of the present disclosure can be identified by drawing a first imaginary line connecting the first intersection point between longitudinal side edge 25A and a leading edge of wing 70 and the fourth intersection point between a trailing edge of wing 60 and the longitudinal side edge 27B. A second imaginary line connecting the second intersection point between longitudinal side edge 25B and a leading edge of wing 60 and the third intersection point between a trailing edge of wing 70 and the longitudinal side edge 27A can also be drawn. An intersection between the first imaginary line and the second imaginary line can provide a useful approximation for the target fluid entry zone.

The wings of the present disclosure comprise various zone/areas which can facilitate orientation and/or placement of the feminine pad within a panty. Bisecting lines will be utilized hereafter to describe the various zones/areas of the wings of the feminine pads in accordance with the present disclosure. In some forms, one or more of the bisecting lines may be co-linear with the lateral centerline 90 of the feminine pad. In some forms, the bisecting lines may be offset from the lateral centerline. For example, one or more of the bisecting lines may be on a first side of the lateral centerline 90—more proximal to the first end. As another example, one or more of the bisecting lines may be on a second side of the lateral centerline 80—more proximal to the second end. As yet another example, one bisecting line may be on a first side of the lateral centerline while a second bisecting line may be on a second side of the lateral centerline. As yet another example, the bisecting lines may be co-linear with each other. And in some forms, the wings described herein are asymmetric about their respective bisecting line.

Figure 1D:
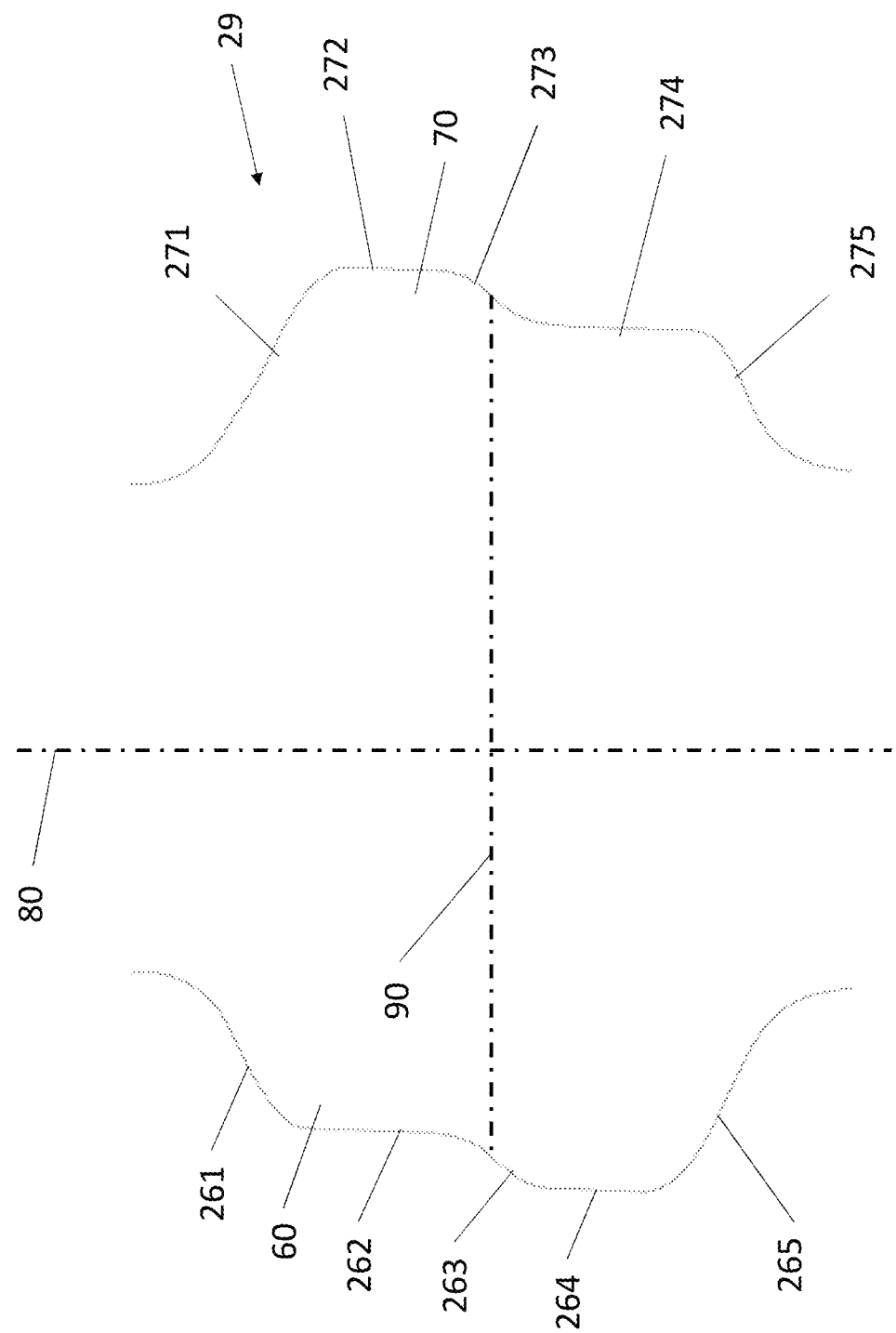
FIG. 1D is an illustration of an intermediate region of the feminine pad of FIG. 1A.

Focusing on the intermediate region 29 in FIG. 1D, the wings 60 and 70 are discussed in additional detail. Each of the wings 60 and 70 comprise an outer periphery defined, in part, by their respective leading edges and trailing edges. Additional edges may be disposed between the leading edges and trailing edges connecting the leading and trailing edges together.

As shown, wing 60 may comprise a leading edge 261 and a trailing edge 265. The leading edge 261 is disposed more proximal to the first end 25 than the second end 27 (each shown in FIG. 1A). Conversely, the trailing edge 265 is disposed more proximal to the second end 27 than the leading edge 261. Each of the leading edge 261 and the trailing edge 265 extend outboard of the chassis 20 and outboard of the longitudinal side edges 25B and 27B (each shown in FIG. 1A).

In some forms, wing 60 may further comprise a first proximal edge 262 which extends from the first leading edge 261 away from the first end 25 and generally parallel to the longitudinal centerline 80. A first transition edge 263 extends from the first proximal edge 262 slightly outboard of the first proximal edge 262 and more proximal to the second end 27. A first distal edge 264 extends from the first trailing edge 265 toward the first end 25 and intersects with the first transition edge 263.

As shown, the first proximal edge 261 and the first distal edge 264 are both disposed outboard of the sides edges 25B and 27B. However, the first distal edge 264 is disposed outboard by a greater extent than the first proximal edge 261. As noted previously, the wings of the present disclosure comprise various zones and areas. Such zones will be described hereafter.

Wing 70 may be configured similarly with regard to wing 60. For example, wing 70 comprises a second leading edge 271 and a second trailing edge 275. The leading edge 271 is disposed more proximal to the first end 25 than the second end 27. Conversely, the trailing edge 275 is disposed more proximal to the second end 27 than the leading edge 271. Each of the leading edge 271 and the trailing edge 275 extend outboard of the chassis 20 and outboard of the longitudinal side edges 25A and 25B (shown in FIG. 1A).

In some forms, wing 70 may further comprise a second distal edge 272 which extends from the second leading edge 271 away from the first end 25 and generally parallel to the longitudinal centerline 80. A second transition edge 273 extends from the second distal edge 272 slightly inboard of the second distal edge 272 and more proximal to the second end 27. A second proximal edge 274 extends from the second trailing edge 275 toward the first end 25 and intersects with the second transition edge 273.

As shown, the second proximal edge 274 and the second distal edge 272 are both disposed outboard of the sides edges 25B and 27B. However, the second distal edge 272 is disposed outboard by a greater extent than the second proximal edge 274. As noted previously, the wings of the present disclosure comprise various zones and areas. Such zones will be described hereafter.

Figure 1E:
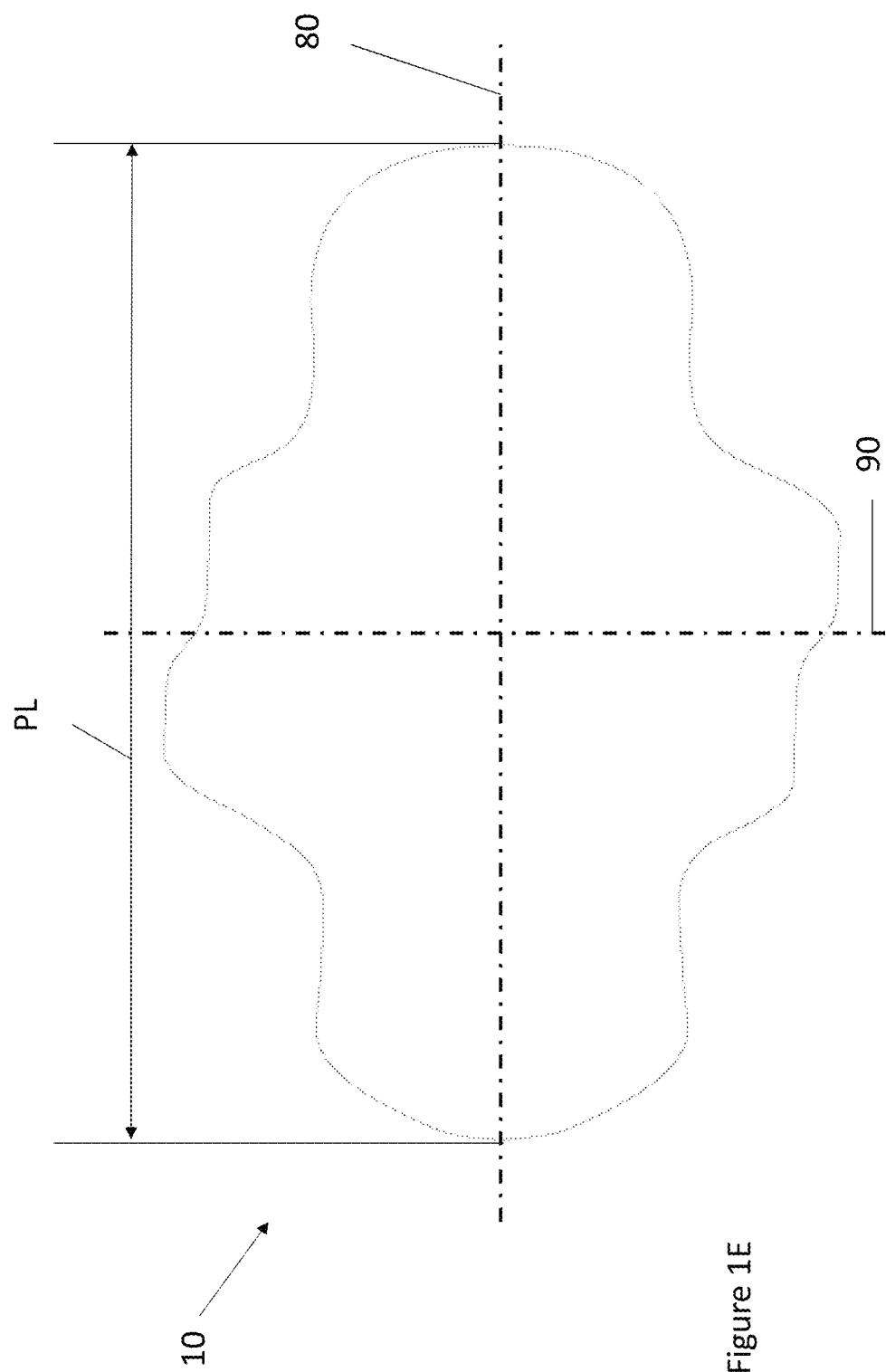
FIG. 1E is an illustration of the feminine pad of FIG. 1A highlighting the pitch length thereof.

Referring to FIG. 1E, the feminine pad 10 may comprise a pitch length PL which is generally parallel to the longitudinal centerline 80. As noted herein, feminine pads may be provided in a variety of sizes to accommodate different loads and to accommodate different times of the day for use. For example, an overnight feminine pad may have a pitch length which is longer than that of a day use feminine pad. In some forms, feminine pads of the present disclosure may have a pitch length PL of between about 200 mm to about 350 mm, from about 220 mm to about 320 mm, or from about 230 mm to about 310 mm, specifically reciting all values within these ranges and any ranges created thereby.

Forms are also contemplated where an array of articles is provided. In such forms, a first plurality of absorbent articles may have a pitch length of between about 210 mm to about 250 mm, from about 220 mm to about 240 mm, or from about 230 mm to about 235 mm, specifically including all values within these ranges and any ranges created thereby. In one particular form, the first plurality of absorbent articles can have a pitch length of about 232 mm. A second plurality of absorbent articles may have a pitch length PL greater than 232 mm. For example, the second plurality of absorbent articles may have a pitch length of from between 240 mm to about 370 mm, from about 260 mm to about 350 mm, or from about 270 mm to about 340 mm, specifically including all values within these ranges and any ranges created thereby. In one particular form, the second plurality of absorbent articles may have a pitch length of about 334 mm. In some forms, a third plurality of absorbent articles may have a pitch length PL of greater than about 232 mm and less than about 334 mm. For example, the third plurality of absorbent articles may have a pitch length PL of about 270 mm or about 274 mm. Forms are contemplated where a fourth plurality of absorbent articles has a pitch length PL of about 300 mm or about 304 mm.

Referring now to FIG. 1F, the feminine pad 10 may comprise a width Ww which is generally parallel to the lateral centerline 90. The width Ww may be greater than about 130 mm, greater than about 140 mm, greater than about 150 mm, greater than about 160 mm, or less than about 180 mm, specifically including all values within these ranges and any ranges created thereby. In one particular form, the width Ww of the pad 10 may be about 156 mm. Forms are contemplated where the width of the pads vary along with pitch length PL. Other forms are contemplated where the width Ww of the pad 10 is constant even though the pitch length varies. Similar to the wing length, when the width Ww of the pad 10 is the same or very close to the same for the variable pitch lengths, this can facilitate application of the pad 10 to the underwear of a user. For example, where the Ww of the pad 10 is the same or very close to the same, e.g. within 20 percent, the user has some familiarity with this width and therefore may not have to greatly adjust how pads are applied to the underwear despite their variable pitch length.

In some forms, a ratio of the width Ww of the pad 10 to the first width Wf can be greater than about 1.5, greater than about 1.6, greater than about 1.7, greater than about 1.9, or greater than about 2.0, specifically including all values within these ranges and any ranges created thereby. In some specific forms, particularly those where Wf and Ww are constant despite pitch length, a ratio of Ww to Wf can be about 1.77. For those forms where either Wf and/or Ww vary along with pitch length PL, the ratios may increase with increasing pitch length. Much like the above, where the ratio of width Ww and Wf remains very close to the same, e.g. within 20 percent, this can facilitate the application of the feminine hygiene article to the underwear of the user.

Figure 2A:
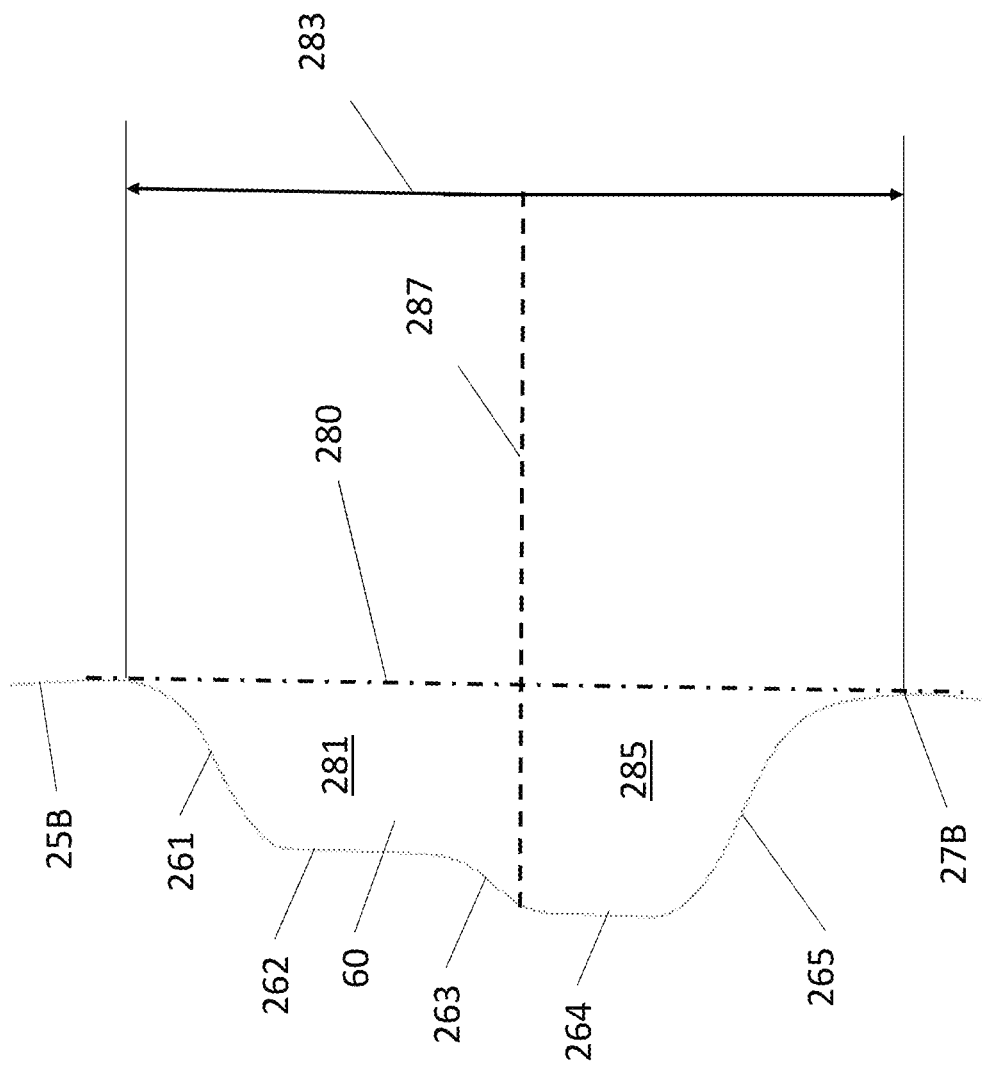
FIG. 2A is an illustration of a first wing of the feminine pad of FIG. 1A.

As shown in FIG. 2A, the wing 60 may have a length 283 which is generally parallel to longitudinal centerline. The length 283 is defined by an intersection of the leading edge 261 and the side edge 25B and an intersection of the trailing edge 265 and the side edge 27B. A bisecting line 287 which bisects the length 283 is generally parallel to the lateral centerline 90 (shown in FIG. 1A) and can serve as a boundary between a first proximal zone 281 and a first distal zone 285. As shown, the bisecting line 287 may intersect the first distal edge 264, the first transition edge 263 or the first proximal edge 262 depending on the design of the wing 60. Additionally, a fold line 280 may be created for the wing 60. The intersections which defines the length 283 similarly defines the endpoints of the fold line 280.

In some forms, for wing 60, the first proximal zone 281 is defined by the first leading edge 261, the first proximal edge 262, the first bisecting line 287, the fold line 280, and depending on the shape of wing 60, the first transition edge 263. In some forms, the first bisecting line 287 may intersect the first proximal edge 262. In such forms, the first transition edge 263 would not form part of the boundary of the first proximal zone 281. In other forms, the first bisecting line 287 may intersect the first distal edge 264. In such forms, the first distal edge 264 would form part of the boundary of the first proximal zone 281. The first distal zone 285 is defined by the first bisecting line 287, the fold line 283, the first trailing edge 265, the first distal edge 264, and depending on the shape of the wing, the first transition edge 263. As shown, the first distal zone 285 may comprise the laterally outermost extents of the wing 60

Wing 70 may be similarly constructed as discussed with regard to wing 60. As shown in FIG. 2B, the wing 70 may have a length 293 which is generally parallel to longitudinal centerline. The length 293 is defined by an intersections of the leading edge 271 and the side edge 25A and an intersection of the trailing edge 275 and the side edge 27A. A second bisecting line 297 which bisects the length 293 is generally parallel to the lateral centerline 90 (shown in FIG. 1A) and can serve as a boundary between a second proximal zone 295 and a second distal zone 291. As shown, the second bisecting line 297 may intersect the second transition edge 273, the second distal edge 272 or the second proximal edge 274. Additionally, a fold line 290 may be created for the wing 70. The intersections which define the length 293 similarly define the endpoints of the fold line 290.

In some forms, for wing 70, the second distal zone 291 is defined by the second leading edge 271, the second distal edge 272, the second bisecting line 297, the fold line 290, and depending on the shape of wing 70, the second transition edge 273. In some forms, the second bisecting line 297 may intersect the second distal edge 272. In such forms, the second transition edge 273 would not form part of the boundary of the second distal zone 291. As shown in FIG. 2B, the second distal zone 291 may comprise the laterally outermost extents of wing 70. In some forms, the second bisecting line 297 may intersect the second proximal edge 274. In such forms, the second proximal edge 274 may form at least a portion of the boundary of the second distal zone 291. The second proximal zone 295 is defined by the second bisecting line 297, the fold line 290, the second trailing edge 275, the second proximal edge 274 and, depending on the shape of the wing, the second transition edge 273.

Referring now to FIGS. 2A and 2B, the length 283 of wing 60 and the length 293 of wing 70 may be equal or at least within about 10 percent of one another. However, forms of the present invention are contemplated where the lengths 283 and 293 of the wings 60 and 70, respectively differ by more than about 20 percent, more than about 30 percent, or more than about 50 percent.

The lengths 283 and 293 of wings 60 and 70, respectively, may be from about 80 to 130 mm, from about 90 to about 120 mm, or from about 100 to about 110 mm. In one particular form, the wing lengths may be about 110 mm. Forms are contemplated where an array of feminine pads is provided wherein each of the pads within the array have different pitch lengths PL but have the same wing length. For example, a ratio of wing length to pitch length may be from about 0.6 to about 0.25, from about 0.5 to about 0.3, specifically including all values within these ranges and any ranges created thereby. In some particular forms, the ratio of wing length to pitch length PL can be about 0.47 for a first plurality of absorbent articles and about 0.36 for a second plurality of absorbent articles. A third plurality of absorbent articles may have a wing length to pitch length PL ratio of less than 0.47 and greater than 0.36.

In such forms, particularly where the wing lengths are constant regardless of pitch length PL, the user's application of the feminine pad to their underwear may be facilitated. For example, even with the longer feminine pads, the wing length consistency among products within the array can allow the user to get used to the application of the wings to the underwear. This can facilitate the application of the feminine hygiene articles to the underwear, whereas variable length wings may inhibit such facilitation.

Figure 3:
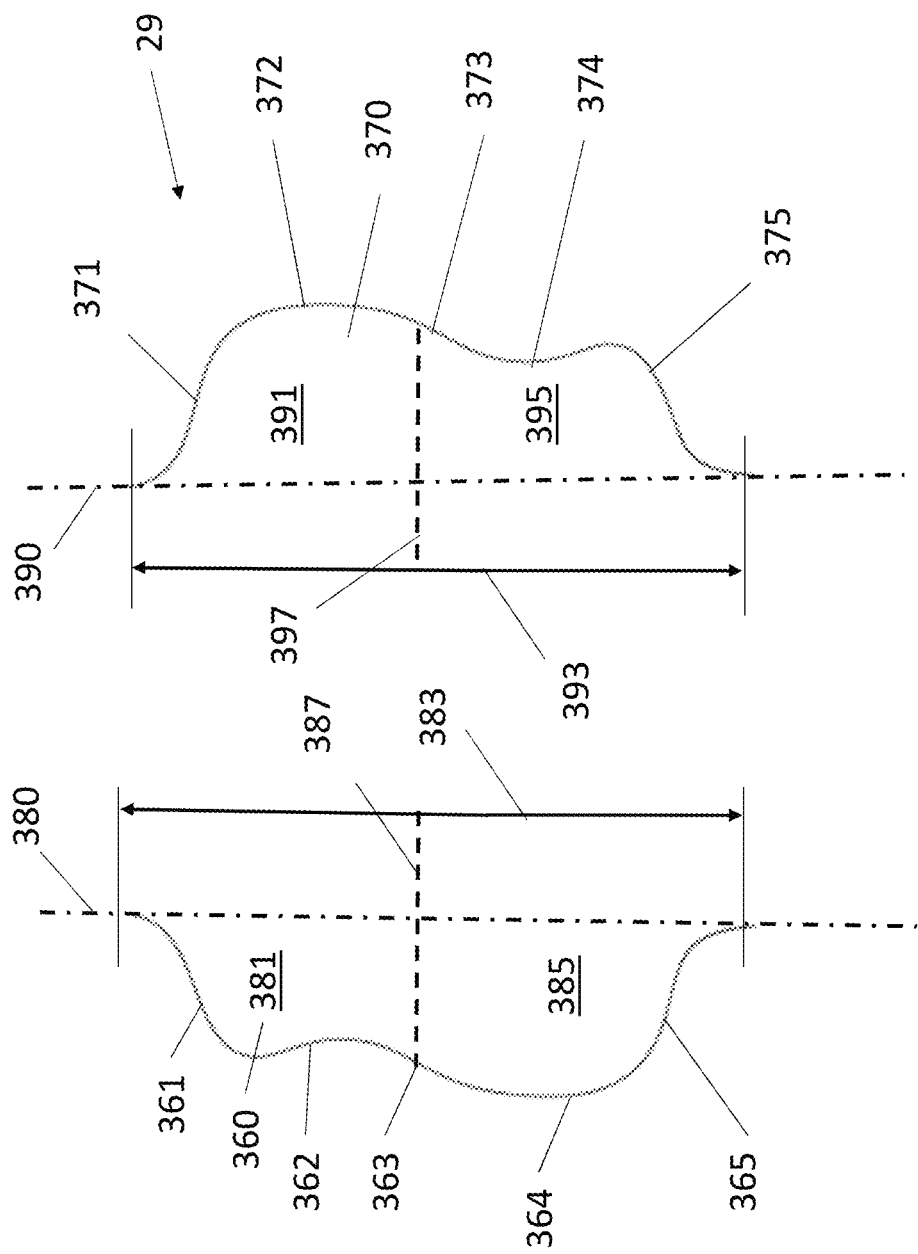
FIG. 3 is an illustration of another form of first and second wings in accordance with the present disclosure.

FIG. 3 depicts another version of the intermediate region 29 of the feminine pad 10 of the present disclosure. Similar to wing 60 discussed above, wing 360 may comprise a first leading edge 361 and a first trailing edge 365. A first proximal edge 362 may extend from the first leading edge 361 toward the first trailing edge 365. However, unlike the first proximal edge 262 (shown in FIGS. 1D and 2A), the first proximal edge 362 may be more curvilinear in nature. A first transition edge 363 may also be much more curvilinear than its counterpart 263 (shown in FIGS. 1D and 2A). A first distal edge 364 extends from the first transition edge 363 and intersects the first trailing edge 365. The zones of wing 360 may be determined similar to the methodology described above.

Wing 370 may comprise a second leading edge 371 and a second trailing edge 375. A second distal edge 372 may extend from the second leading edge 371 toward the second trailing edge 375. However, unlike the second distal edge 272 (shown in FIGS. 1D and 2B), the second proximal edge 372 may be more curvilinear in nature. A second transition edge 373 may also be much more curvilinear than its counterpart 273 (shown in FIGS. 1D and 2B). A second proximal edge 374 extends from the second transition edge 373 and intersects the second trailing edge 375. The zones of wing 370 may be determined similar to the methodology described above.

For example, a length 383 of wing 360 may be determined by the intersection of the first leading edge 361 and the side edges of the chassis and the intersection of the first trailing edge 365 and the side edges of the chassis. The length 383 is generally parallel to the longitudinal centerline 80 (shown in FIG. 1A). A first bisecting line 387 which bisects the length 383 may extend generally parallel to the lateral centerline 90 (shown in FIG. 1A) and may intersect the first transition edge 363. In some forms, the first bisecting line 387 may intersect the first proximal edge 362 or the first distal edge 364, depending on the design of the wing 360.

As shown, a first proximal zone 381 of wing 360 may be bounded by the first leading edge 361, the first proximal edge 362, the first bisecting line 387, the first fold line 380, and depending on the shape of the wing 360 the first transition edge 363. In some forms, the bisecting line 387 may intersect the first distal edge 364. In such forms, the first distal edge 364 may form a portion of the first proximal zone 381. In other forms, the bisecting line 387 may intersect the first proximal edge 362, in such forms, the first transition edge 363 may not form a portion of the first proximal zone 381.

A first distal zone 385 may be defined by the first trailing edge 365, the first distal edge 364, the first bisecting line 387, the fold line 383, and depending on the shape of the wing, the first transition edge 363. The first distal zone 385 may comprise the laterally outermost extents of the wing 360.

A wing 370 may be configured similarly to the wing 360. Namely, the wing 370 may comprise a length 393 which is determined by the intersection of the second leading edge 371 and the side edges of the chassis and the intersection of the second trailing edge 375 and the side edges of the chassis. A second bisecting line 397 extends from the fold line 393 generally parallel to the lateral centerline 90 (shown in FIG. 1A) and intersects the second distal edge 372. In some forms, the second bisecting line 397 may intersect the second proximal edge 374 or the second transition edge 363, depending on the design of the wing 370.

A second distal zone 391 and a second proximal zone 395 may be defined, in part, by the second bisecting line 397. The second distal zone 391 may comprise the laterally outermost extents of the wing 370. The second distal zone 391 may be defined by the second leading edge 371, the second distal edge 372, the second bisecting line 397, the fold line 393, and depending on the shape of the wing 370, the second transition edge 373. In some forms, the second bisecting line 397 may intersect the first distal edge 372. In such forms, the second transition edge 373 would not form part of the boundary of the second distal zone 391. In other forms, the second bisecting line 397 may intersect the second proximal edge 374. In such forms, the second proximal edge 374 may form a portion of the boundary of the second distal zone 391.

A second proximal zone 395 may similarly be created by the second bisecting line 397. The second proximal zone 395 may be defined by the second trailing edge 375, the second proximal edge 374, the second bisecting line 397, the fold line 393, and depending on the shaped of the wing, the second transition edge 373.

Figure 4:
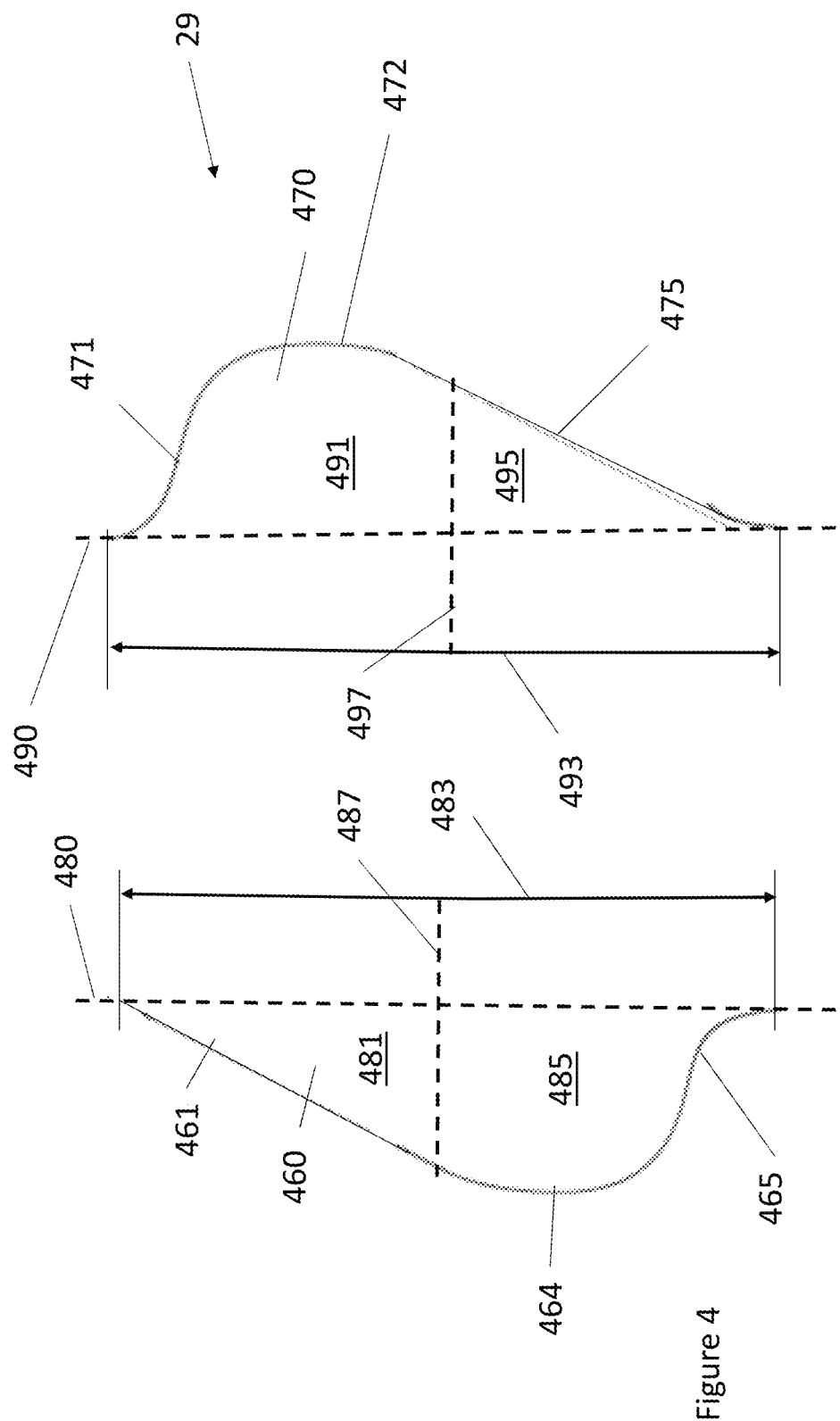
FIG. 4 is an illustration of another form of first and second wings in accordance with the present disclosure.

FIG. 4 depicts yet another version of the intermediate region 29 of the feminine pad 10 of the present disclosure. As shown wing 460 may comprise a leading edge 461 which extends from side edges of the chassis toward the second end of the feminine pad. As shown, the leading edge 461 may extend toward the second end of the feminine pad and also extend outboard of the chassis. However, in the form shown, the wing 460 may not comprise a first proximal edge like the forms discussed heretofore. Instead, the first leading edge 461 may transition into a first distal edge 464. And, the first distal edge 464 may transition into a first trailing edge 465 which joins the first distal edge 464 and the chassis.

A length 483 of wing 460 may be determined by the intersection of the first leading edge 461 and the side edges of the chassis and the intersection of the first trailing edge 465 and the side edges of the chassis. The length 483 is generally parallel to the longitudinal centerline 80 (shown in FIG. 1A). A first bisecting line 487 which bisects the length 483 may extend generally parallel to the lateral centerline 90 (shown in FIG. 1A) and may intersect the first leading edge 461 or the first distal edge 464, depending on the design of the wing 460.

As shown, a first proximal zone 481 of wing 460 may be bounded by the first leading edge 461, the first bisecting line 487, and the first fold line 480. In some forms, the bisecting line 487 may intersect the first distal edge 464. In such forms, the first distal edge 464 may form a portion of the first proximal zone 481. A first distal zone 485 may be defined by the first trailing edge 465, the first distal edge 464, the first bisecting line 487, and the fold line 480. The first distal zone 485 may comprise the laterally outermost extents of the wing 460.

Wing 470 may comprise a second leading edge 471 and a second trailing edge 475. A second distal edge 472 may extend from the second leading edge 471 to the second trailing edge 475. A length 493 of wing 470 may be determined by the intersection of the second leading edge 471 and the side edges of the chassis and the intersection of the second trailing edge 475 and the side edges of the chassis. The length 493 is generally parallel to the longitudinal centerline 80 (shown in FIG. 1A). A second bisecting line 497 which bisects the length 493 may extend generally parallel to the lateral centerline 90 (shown in FIG. 1A) and may intersect the second trailing edge 475 or the second distal edge 472, depending on the design of the wing 470.

A second distal zone 491 and a second proximal zone 495 may be defined, in part, by the second bisecting line 497. The second distal zone 491 may comprise the laterally outermost extents of the wing 470. The second distal zone 491 may be defined by the second leading edge 471, the second distal edge 472, the second bisecting line 497, and the fold line 490. In some forms, the second bisecting line 497 may intersect the second distal edge 472. The second proximal zone 495 may similarly be created by the second bisecting line 497. The second proximal zone 495 may be defined by the second trailing edge 475, the second bisecting line 497, the fold line 490, and depending on the shape of the wing, the second distal edge 472.

As shown in FIGS. 1A-4, the wings are asymmetric with respect to each other. Such asymmetry can contribute to the overall indication of the correct placement and correct orientation of the feminine pad within the panty. And, as noted previously, the correct placement and correct orientation can allow the absorbent core and other portions of the feminine pad to function with more efficacy than if improperly placed or oriented.

For each of the wings shown in FIGS. 2A-4, each is asymmetric about its bisecting line. Again, this asymmetry can help facilitate application of the pad to the panty. And, such asymmetry can similarly facilitate removal of the pad from the panty as described herein. As shown, each of the distal zones has a larger surface area than their respective proximal zones.

Proper Attachment of the Pad

In order to facilitate fastening the wings onto the panty of a wearer, the wearer should be appropriately apprised regarding where to grasp the wings. Improper handling of the wings could produce wrinkles in the wings during fastening. These wrinkles can cause discomfort and may lead to premature detachment of the feminine pad from the panty. For example, referring back to FIGS. 2A and 2B, if the user were to grasp either the wing 60 or 70 in the first proximal zone 281 or the second proximal zone 295, respectively, wrinkles could be created in each of the wings 60 and 70. The inventors have found that the better approach to reduce the likelihood of wrinkles within the wings during fastening occurs when the wings are grasped by their respective distal zones. Because the distal zones extend outboard to a further extent than does the proximal zones, the distal zones can more easily manipulate the proximal zones. While grasping each of the wings at two different longitudinal locations may seem counterintuitive, such application can enhance the experience provided to the wearer during use. For example, as noted previously, such application can reduce the likelihood of wrinkles in the wings which can enhance the comfort to the user.

In order to advocate proper application of the wings to the panty, visual signals may be employed which help provide an indication of where to grasp the wings. For example, referring to FIGS. 2A and 2B, in some forms, embossing may be provided in the first distal zone 285 of wing 60 and the first distal zone 291 in wing 70. As another example, a visual signal may comprise printing in the first distal zone 285 of wing 60 and in the second distal zone 291 of wing 70. In yet another example, a visual signal may comprise a combination of printing and embossing in the first distal zone 285 and the second distal zone 291.

To avoid confusion during the application of the wings 60 and 70, the density of the visual signals on the wings 60 and 70 should be higher in the first distal zone 285 and second distal zone 291 than in the first proximal zone 281 and the second proximal zone 295, respectively. For example, where the visual signal comprises embossing, the level of embossing in the first distal zone 285 should be higher than the level of embossing in the first proximal zone 281. In such examples, the amount of surface area of the respective zones may be compared to determine which zone has a higher level of embossing. Where the visual signal comprises printing, the amount of surface area of the respective zones may be compared to determine which zone has a higher level of printing thereon. Where the visual signal comprises a combination of embossing and printing, the amount of surface area of the respective zones may be compared to determine which zone has a higher level of embossing or printing.

In some specific forms, the visual signal may be more direct and may not subscribe to the above. For example, in some forms, the visual signal may comprise an arrow or something similar which connotes a direction which is disposed adjacent to the intersection between the first trailing edge 265 and the first distal edge 264 or the intersection between the second leading edge 271 and the second distal edge 272. In such forms, the visual signal may need to be placed within 10 mm within 8 mm, within 6 mm, or within 5 mm of the first distal edge 264 of the wing 60 and/or the second distal edge 272 of the wing 70 specifically including any values within these ranges and any ranges created thereby.

While alternative wing configurations are contemplated, without implementation of the above visual signal, the application of the wings could lead to wrinkles and or other asperities in application of the feminine pad. And as stated before, such wrinkles may lead to premature detachment of the pad from the panty or may preclude attachment to the panty altogether. Alternative wing configurations are provided with regard to FIGS. 3 and 4.

Figure 5:
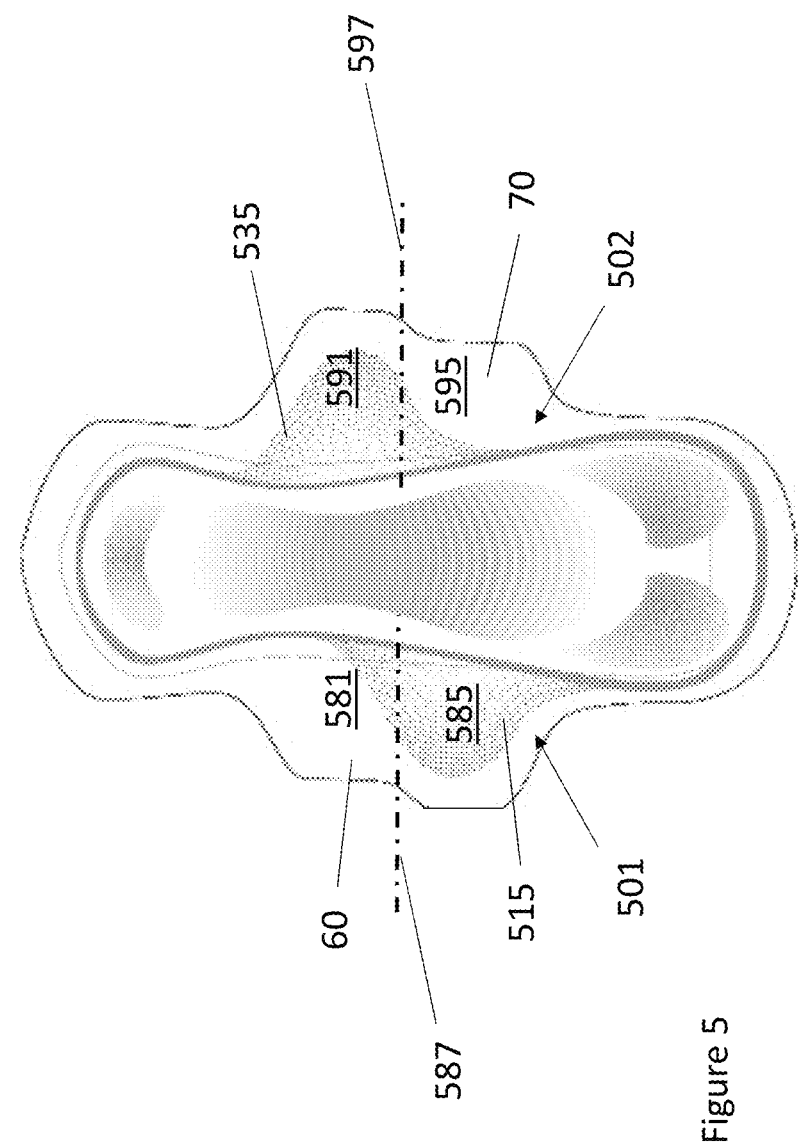
FIG. 5 is an illustration of a feminine pad comprising a visual signal in accordance with the present disclosure.

An example of a visual signal provided on the wings of the feminine pads of the present disclosure is provided with regard to FIG. 5. As previously discussed, the distal zones may comprise a higher amount of visual signaling than their proximal zone counterparts. Such signaling can facilitate the application of the feminine pad 10 (shown in FIG. 1A) by prompting a user to grasp the wings 60, 70, 360, 370, 460, and 470 (shown in FIGS. 1A-4), in the appropriate locations for fastening about the panty of the wearer. Methods for measuring the amount of visual signaling are disclosed herein. Note that bisecting lines 587 and 597 have been provided which approximates a boundary between distal and proximal zones for the wings 60 and 70, respectively.

As shown, a print signal 515 may be disposed on a first surface 501 of wing 60 primarily in a distal zone 585 of the wing 60. While the print signal 515 may also exist in a proximal zone 581 of wing 60, a larger area of print is provided in the distal zone 585 of the wing 60.

Wing 70 may be similarly configured. For example, a print signal 535 may be disposed, primarily, on a first surface 502 in a distal zone 591 of the wing 70. While the print signal 535 may also exist in a proximal zone 595 of wing 70, a larger area of print is provided in the distal zone 595 of the wing 70.

And as stated previously, the visual signals described herein are not limited to print signals. In some forms, embossing may be utilized to provide the indication described herein. In other forms, a combination of print and embossing may be utilized. In other forms, different colored materials, e.g. dyed materials, may be utilized to signal to the user where to grasp.

Figure 6:
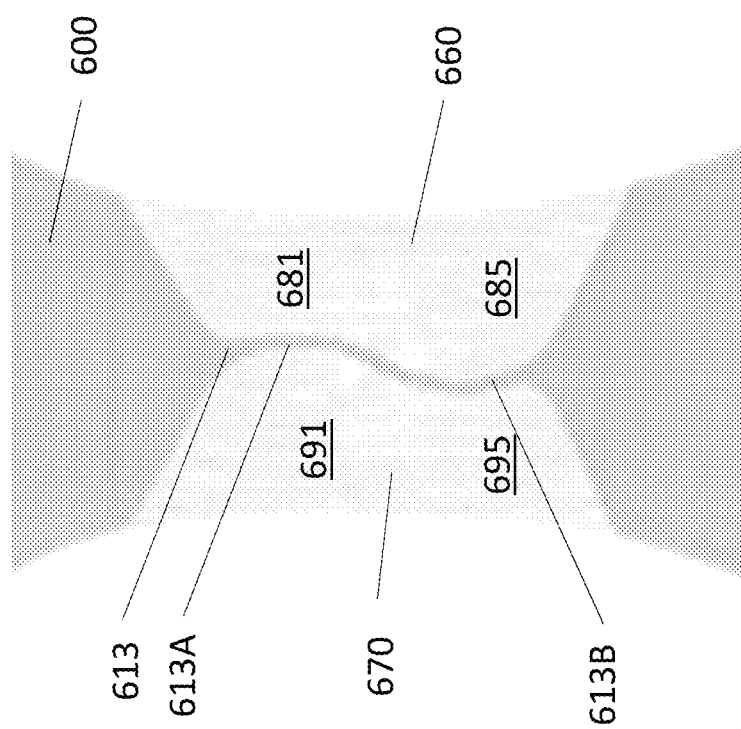
FIG. 6 is an illustration of a feminine pad attached to a panty with wings wrapped around the panty.

The wings, in a fastened configuration, can provide another visual attribute indicating proper attachment to the panty. FIG. 6 is a depiction of a pair of wings 660 and 670 in a fastened configuration wrapped around a panty 600. As shown, wings 660 and 670 appear to nest when fastened to the panty. Specifically, a second distal zone 691 nests with a first proximal zone 681. And similarly, a first distal zone 685 nests with a second proximal zone 695.

The wings 670 and 660 may be designed such that for normal panties (excludes tanga underwear) the wings 660 and 670 do not overlap in use. As such, a gap 613 may exist between the wings 660 and 670 during use. A gap 613 may be highly variable as users can apply the wings of the present disclosure in a variety of different configurations and as panty crotch widths can vary greatly. For example, some users may attach the pad of the present disclosure to their panty such that the wings have a 0 mm gap between the wings. As another example, some users may fasten the wings to the panty such that the wings are broadly spaced apart, e.g. 3 mm, 5 mm, 7 mm, or 10 mm.

Additionally, the gap 613 can provide a visual indication of when the feminine pad is skewed with respect to the panty 600. For example, where the second distal zone 691 overlaps or contacts the first distal zone 685, this can indicate that the pad is skewed with respect to the panty 600. As another example, where the gap 613 has an uneven width from a first offset portion 613A to a second offset portion 613B, this can indicate skew with regard to the pad with respect to the panty 600. And, while a user may not be able to visualize the orientation of the wings 660 and 670 on the underside of the panty 600 during application, the gap 613 can provide a tactile cue to the user as to whether the pad is skewed with respect to the panty 600.

Additionally, the gap 613 may facilitate removal of the feminine pad. Where wings overlap, wing adhesive can adhere one wing to another of the wings. This can increase the difficulty of separating the wings from the panty during removal. Generally, in this scenario, a user would have to separate the wings from one another prior to removal of the wings from the panty.

As shown, the gap 613 may comprise offset portions 613A and 613B. As shown, portion 613A may be offset from the longitudinal centerline 80 (shown in FIG. 1A) in a first direction, and portion 613B may be offset from the longitudinal centerline 80 (shown in FIG. 1A) in a second direction which is opposite the first direction. In some forms, the first portion 613A may be aligned with the longitudinal centerline 80 (shown in FIG. 1A) while the second portion 613B may be offset from the longitudinal centerline 80 (shown in FIG. 1A). In other forms, the first portion 613A may be offset with respect to the longitudinal centerline 80 (shown in FIG. 1A) while the second portion 613B is aligned with the longitudinal centerline 80 (shown in FIG. 1A).

Sustaining Coverage

In addition to providing assistance with the proper orientation of the pad, the shape of the wing can also play a large part in sustaining coverage and maintaining attachment to the panty. For example, wings of the present disclosure may be configured such that an adequate amount of fastening adhesive is provided to the wings so that the wings can maintain adherence to the panty. At the same time, a careful balance should be achieved. For example, too much adhesive can make the removal of the pad from the panty a much more arduous task. In contrast too little adhesive or ill placed adhesive can cause premature detachment of the pad from the panty.

Figure 7A:
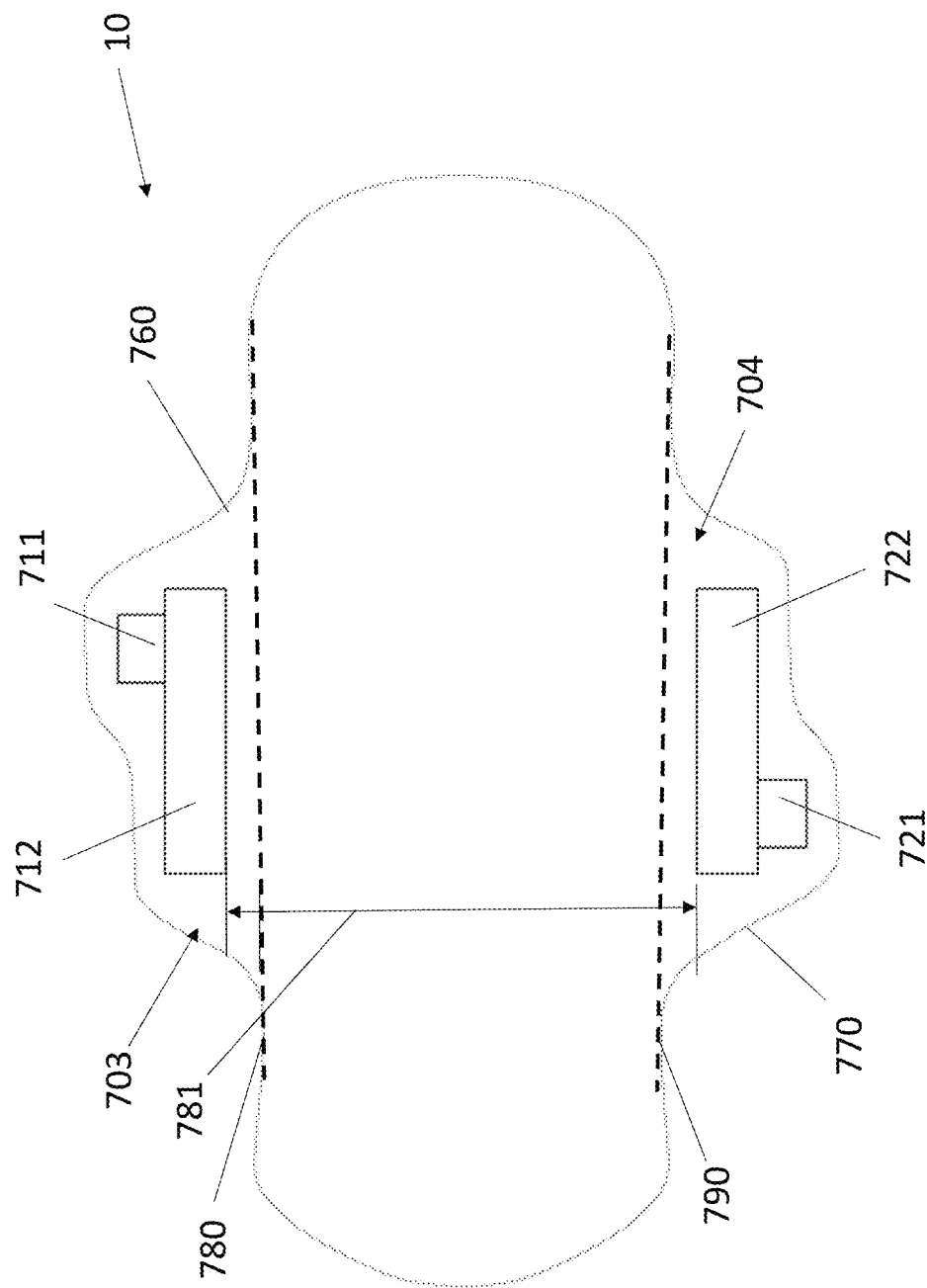
FIG. 7A is an illustration of an underside of a feminine pad in accordance with the present disclosure.

Referring to FIG. 7A, in addition to the visual signaling discussed herein, the dimensions of the distal zones can be an important aspect of the feminine pads of the present invention as well as the adhesive placement on the wings. The underneath side of the feminine pad 10 is depicted with adhesive areas 711 and 712 on a second surface 703 of wing 760 and adhesive areas 721 and 722 on a second surface 704 of wing 770.

Focusing on wing 760, the adhesive areas 711 and 712 help secure the wing 760 to the panty in use. However, if the adhesive areas 711 and 712 are misapplied to the wing 760, then the wing 760 may become more susceptible to detachment during wear. So, the adhesive areas 711 and 712 should be carefully placed upon the wing 760.

Figure 7B:
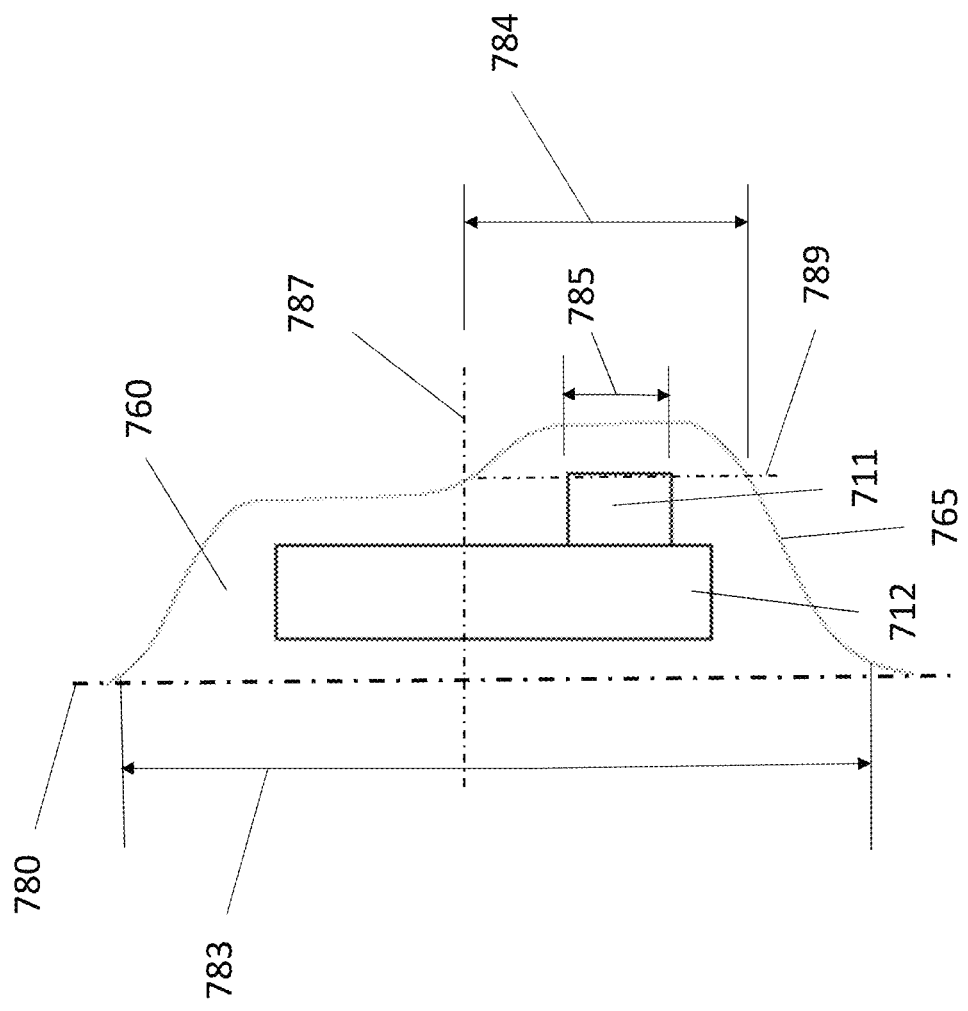
FIG. 7B is an illustration of a first wing of the feminine pad of FIG. 7A.

As shown in FIG. 7B, the wing 760 comprises a length 783 which can be determined as described heretofore with regard to lengths associated with wings 60 and 70 (shown in FIGS. 2A and 2B, respectively). A bisecting line 787— generally parallel to the lateral centerline 90 (shown in FIG. 1A) bisects the length 783. A first guide line 789 is drawn from an intersection between the bisecting line 787 and an edge of the wing 760, e.g. first leading edge, first transition edge, or the first distal edge. The first guide line 789 extends perpendicular to the bisecting line 787 and extends parallel to the longitudinal centerline 90 (shown in FIG. 1A). The first guide line 789 should extend into the distal zone or through the distal zone if its origin is already there such that the majority of the first guide line 789 resides in the distal zone of the wing 760. For wing 760, this may mean that the first guide line 789 will extend in a direction which is toward the second end of the feminine pad.

A distal zone adhesive length 784 is defined by the intersection between the bisecting line 787 and the first guide line 789 and an intersection between the first guide line 789 and a trailing edge 765 of wing 760. An adhesive length 785 is generally parallel to the longitudinal centerline 90 (shown in FIG. 1A). The adhesive length 785 is determined by the outermost extents of the adhesive area 711 that are disposed on the wing 760.

A ratio of the distal zone adhesive length 784 to the adhesive length 785 can be important in ensuring that the wings do not prematurely detach and in ensuring that the wings are easy to attach and remove. For example, if the ratio is too high, then much of the distal zone of wing 760 remains without adhesive and can become prematurely detached during use. In contrast, if the ratio is too small, the user may not have a sufficient area to grasp the wing 760 during removal. Additionally, if the ratio is too small, the adhesive areas 711 and 712 may extend beyond the edges of the wings frustrating the application and removal of the pad from the panty.

Where the ratio is small, pad converting processes may need to be adjusted to ensure that the likelihood of adhesive areas 711 or 721 extending beyond the edges of the wings is minimized. For example, during processing, webs often track (move in a cross direction and machine direction). Web tracking can impact the placement of the adhesive areas on the wings. As another example, adhesive may be applied to the wings via a carrier sheet. There is variability of the adhesive application to the carrier sheet which can in turn impact the location of the adhesive areas on the wings. And, prior to packing the feminine pad, the wings are typically folded over a topsheet of the feminine pad. There is variability in the folding operation which can impact the placement of the adhesive on the wings.

Based on the foregoing, a balance should be achieved regarding the ratio of the distal zone adhesive length 784 to the adhesive length 785 to ensure that adequate adhesive coverage is achieved along with facilitated removal when desired. In some forms the ratio of the distal zone adhesive length 784 to the adhesive length 785 may be between about 1.15 to about 4.6, about 1.27 to about 2.25, or about 1.38 to about 2.0, specifically including any values within these ranges and any ranges created thereby.

Figure 7C:
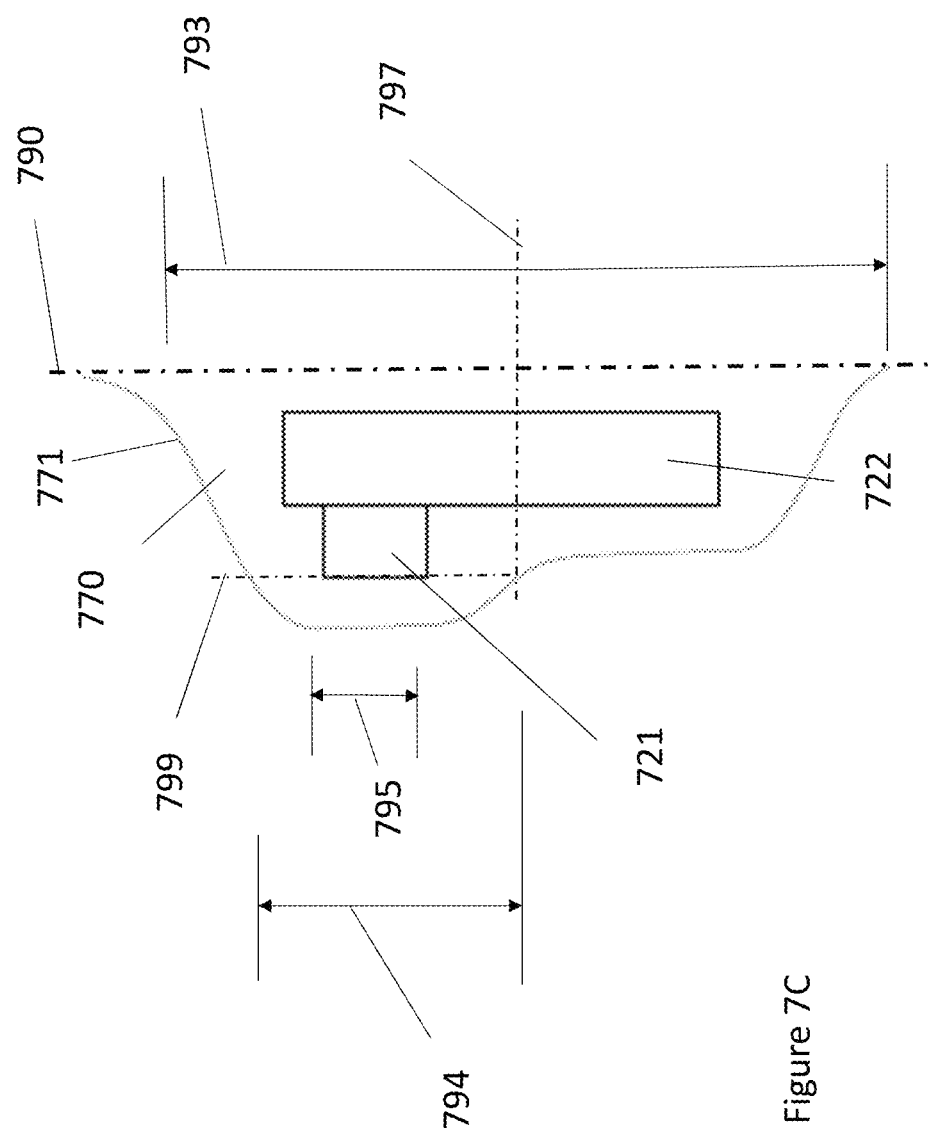
FIG. 7C is an illustration of a second wing of the feminine pad of FIG. 7A.

As shown in FIG. 7C, the wing 770 comprises a length 793 which can be determined as described heretofore with regard to lengths associated with wings 60 and 70 (shown in FIGS. 2A and 2B, respectively). A bisecting line 797— generally parallel to the lateral centerline 90 (shown in FIG. 1A)—bisects the length 793. A second guide line 799 is drawn from an intersection between the bisecting line 797 and an edge of the wing 770, e.g. second leading edge, second transition edge, or the second distal edge. The second guide line 799 extends perpendicular to the bisecting line 797 and extends parallel to the longitudinal centerline 90 (shown in FIG. 1A). The second guide line 799 should extend into the distal zone or through the distal zone if its origin is already there such that the majority of the first guide line 799 resides in the distal zone of the wing 770. For wing 770, this may mean that the second guide line 799 will extend in a direction which is toward the first end of the feminine pad.

A distal zone adhesive length 794 is defined by the intersection between the bisecting line 797 and the second guide line 799 and an intersection between the second guide line 799 and a leading edge 771 of wing 760. An adhesive length 795 is generally parallel to the longitudinal centerline 90 (shown in FIG. 1A). The adhesive length 795 is determined by the outermost extents of the adhesive area 721 that are disposed on the wing 770. A ratio of the distal zone adhesive length 794 to the adhesive length 795 can be within the ranges described heretofore with regard to wing 760.

Referring now to FIGS. 7A-7C, as shown, in some forms, the adhesive area 711 may be asymmetrically disposed with respect to the bisecting line 787. In some forms, the adhesive area 712 may also be disposed asymmetrically with respect to the bisecting line 787 in conjunction with adhesive area 711. Similarly, in some forms, the adhesive area 721 may be asymmetrically disposed with respect to the bisecting line 797. Similarly, in some forms, the adhesive area 722 may be asymmetrically disposed with respect to the bisecting line 797 in conjunction with adhesive area 721.

Figure 8:
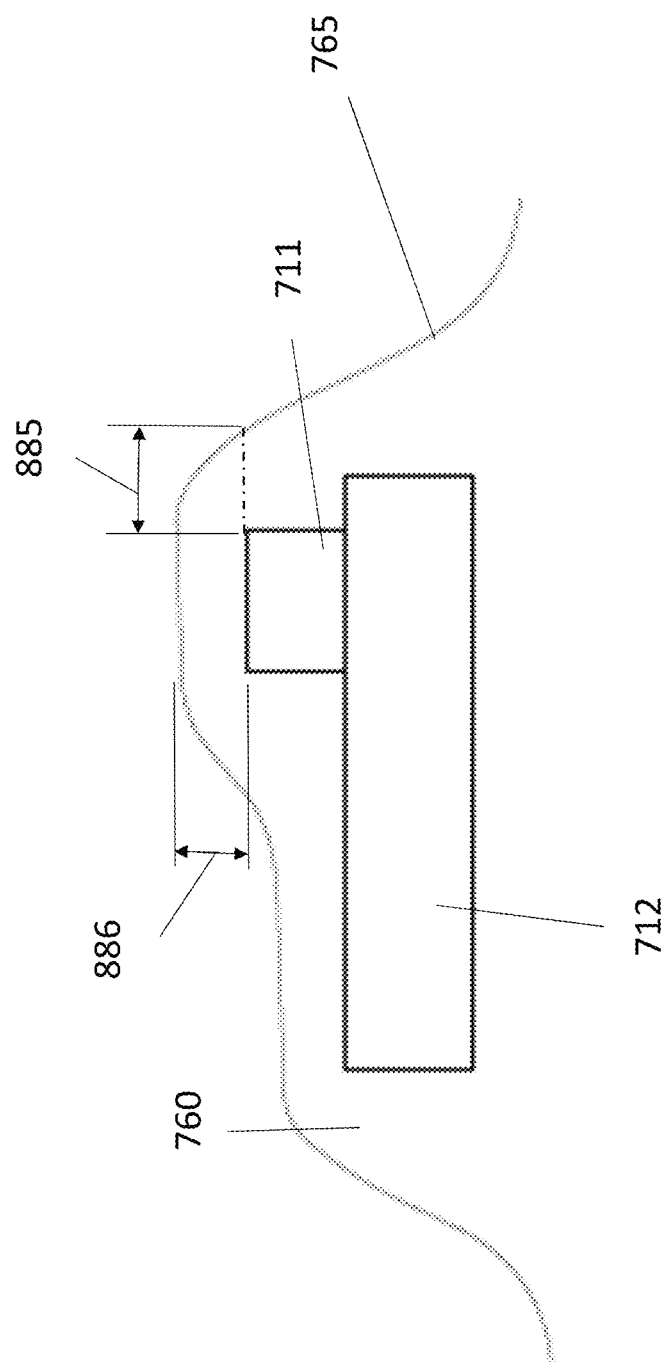
FIG. 8 is an illustration showing a close up view of the first wing of FIG. 7B.

Referring to FIGS. 7B-8, spacing of the adhesive area 711 from the trailing edge 765 (or the leading edge if wing 770) may be of import in addition to the ratios discussed above. For, example, as noted previously, where the adhesive area 711 extends to the edges of the wing 760 or 770, the wing may prove difficult to remove from the panty. Instead, the inventors have found that a small handle (an area free of adhesive) can facilitate removal. A leading edge/trailing edge spacing 885 (generally parallel to the longitudinal centerline 80 (shown in FIG. 1A)) can be about 2 mm to about 9 mm, about 3 mm to about 7 mm, or from about 4 mm to about 6 mm specifically including any values within these ranges and any ranges created thereby.

Similar spacing considerations may be taken into account regarding a distal edge spacing 886. The distal edge spacing 886 is generally parallel to the lateral centerline 80 (shown in FIG. 1A). Similar to the leading edge/trailing edge spacing 885, the distal edge spacing 886 may be about 2 mm to about 9 mm, about 3 mm to about 7 mm, or from about 4 mm to about 6 mm specifically including any values within these ranges and any ranges created thereby.

Referring now to FIGS. 5 and 7A, as noted previously, the first print signal 515 and the second print signal 535 can provide the user with the appropriate indication about where to grasp the wings for proper attachment to the panty. Additionally, though, the first print signal 515 and the second print signal 535 can provide the user with appropriate indication of where the adhesive areas are on the second surface of the wing. For example, the first print signal 515 may correspond to the first adhesive area 711 on second surface 703 of the first wing 760 such that at least a portion of the first adhesive area 711 is disposed within the projection of the first print signal 515 area through the first wing 760. In some forms, at least 50 percent of the first adhesive area 711 is disposed within the projected area of the first print signal 515, at least 75 percent of the first adhesive area 711, or at least 100 percent of the first adhesive area 711, specifically including all values within these ranges and any ranges created thereby.

Referring back to FIG. 7A, another factor of import is the spacing of the adhesive areas 712 and 722 from folding lines 780 and 790 for wings 760 and 770, respectively. The adhesive area 712 should be spaced adequately from the folding line 780 to ensure that the adhesive area 712 does not overlap or lie on the panty leg elastics in the fastened position. Similarly, the adhesive area 722 should be adequately spaced from the folding line 790 to ensure that the adhesive area 722 does not overlap or lie on the panty leg elastics in the fastened position. To accommodate this aspect, the adhesive areas 712 and 722 may be spaced apart from one another by a distance 781. In some forms, the adhesive areas 712 and 722 may have a space between them having a width 781 of from 70 mm to 120 mm, about 80 mm to 110 mm, or about 97.5 mm to about 102 mm, specifically including any values within these ranges and any ranges created thereby.

Without such spacing of the adhesive areas 712 and 722, the leg elastics of the panty could be rendered basically useless as the adhesive effectively locks the elastics in place. This can cause discomfort. Additionally, because the leg elastics are designed to flex and move with the wearer, during use, the leg elastics may prematurely cause the adhesive areas 712 and 722 to become detached from the panty. This detachment can further lead to premature detachment of the adhesive areas 711 and 721.

Another variable of import regarding sustained attachment to the panty is with regard to a grasping area versus coverage areas of the wings. In general, a ratio of coverage areas should be about equal. If the ratio of areas becomes unbalanced, then premature detachment of the pad from the panty can occur.

Figure 9A:
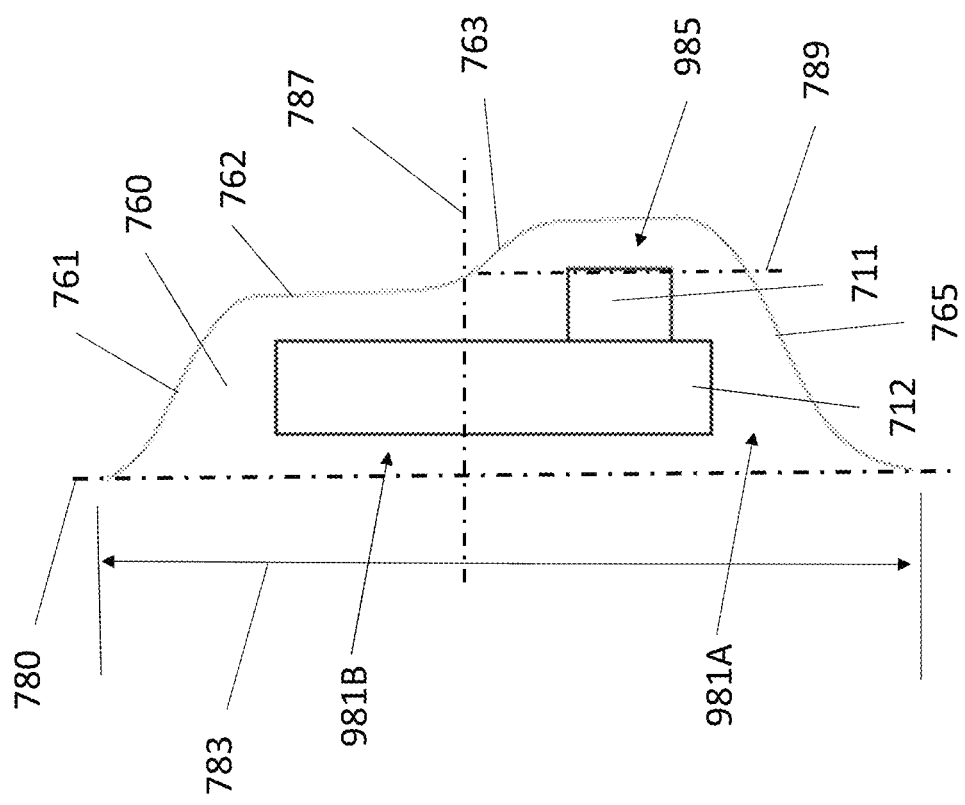
FIG. 9A is an illustration of the first wing in FIG. 7B further showing coverage areas and a grasping area.

Referring to FIG. 9A, the first guide line 789 associated with adhesive area 711 is helpful in determining a grasping area 985 versus the coverage areas 981A and 981B. The first guide line 789 can create a boundary for the grasping area 985, a first coverage area 981A, and a second coverage areas 981B on the wing 760. As shown, the first coverage area 981A is bounded by the first trailing edge 765, the first guide line 789, the bisecting line 787, and the fold line 780. The second coverage area 981B is bounded by a first leading edge 761, a first proximal edge 762, the bisecting line 787 and the fold line 780. In some forms, the first coverage area 981A and the second coverage area 981B are about the same size.

Figure 9B:
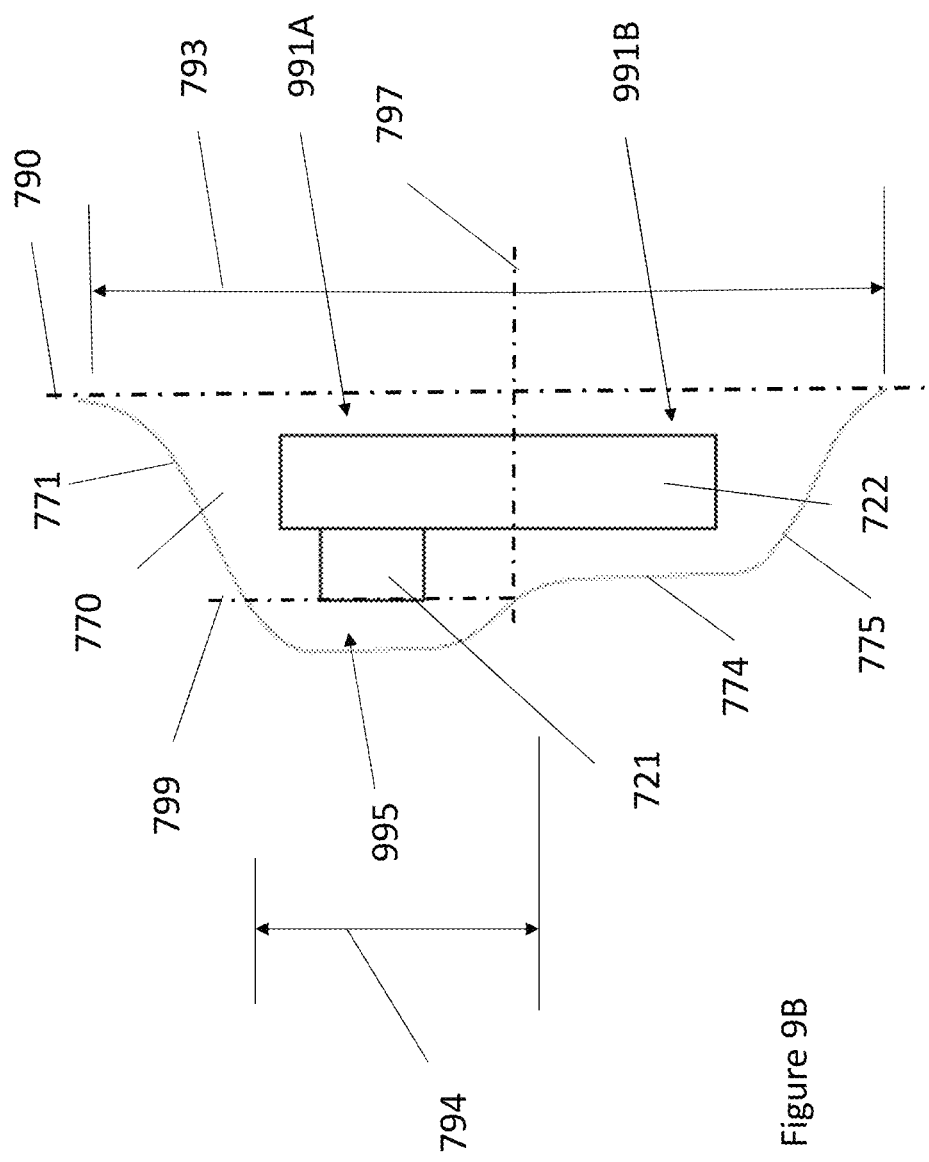
FIG. 9B is an illustration of the second wing of FIG. 7C further showing coverage areas and a grasping area.

Referring to FIG. 9B, the second guideline 799 is helpful in determining a grasping area 995 and coverage areas 991A and 991B for the wing 770. The second guide line 799 can create a boundary for the grasping area 995, the first coverage area 991A and the second coverage area 991B on the wing 770. As shown, the first coverage area 991A is bounded by the second leading edge 771, the second guide line 799, the bisecting line 797, and fold line 790. Similarly, the second coverage area 991B is bounded by a second trailing edge 775, a second proximal edge 774, the bisecting line 797, and fold line 790. In some forms, the first coverage area 991A and the second coverage area 991B are about the same size.

It is worth noting that the first guide line 789 and the second guide line 799, in some forms, can form a portion of a boundary for the second coverage areas 981B and 991B. Depending on the placement of the adhesive areas 711 and 721, the first guide line 789 and/or second guide line 799 may be disposed inboard to a larger extent than shown in FIGS. 9A and 9B, respectively. In such forms, the grasping areas 985 and 995 would form the outermost portions of the wings 760 and 770.

Figure 9C:
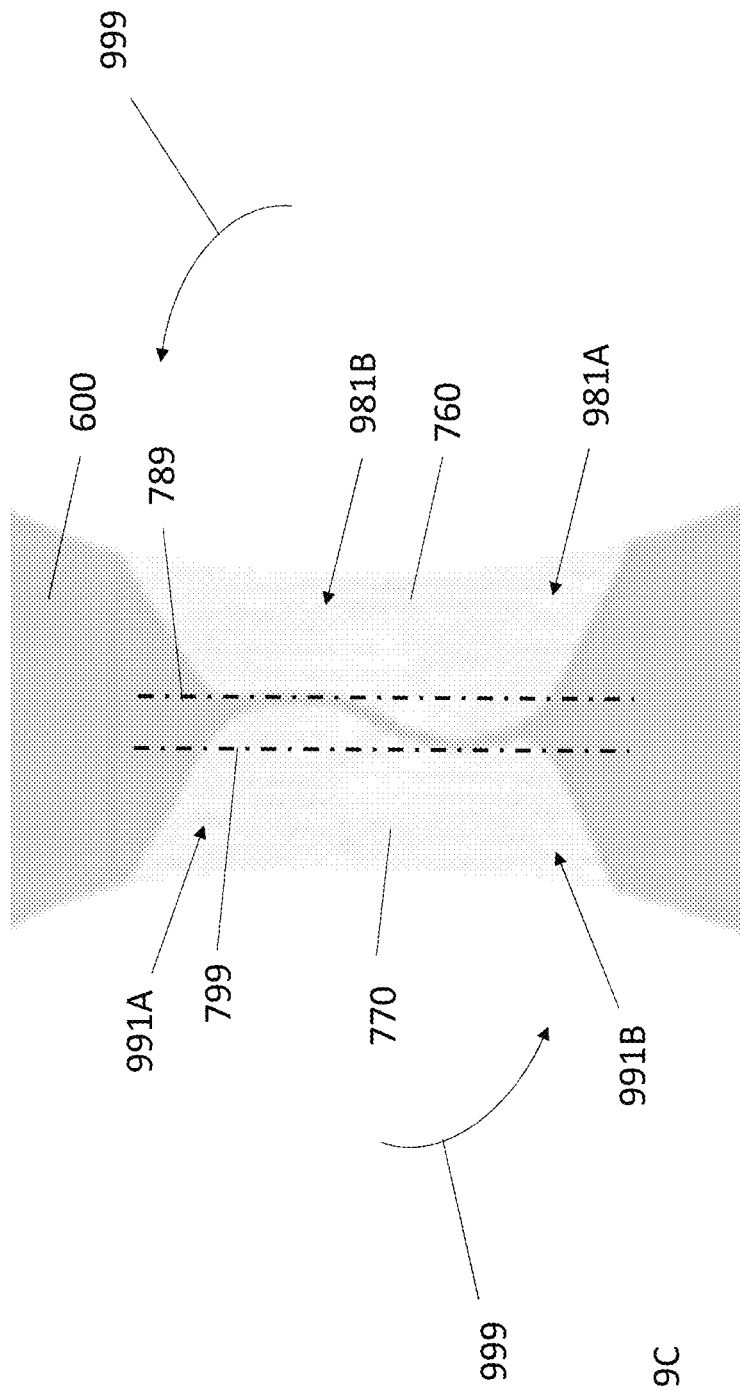
FIG. 9C is an illustration of wings wrapped around a panty and also showing coverage areas of the wings.

As noted previously, the surface area of the first coverage area and the second coverage area should be similar. In some forms, the ratio between the first coverage area and the second coverage area can be about 1 to 1.48, about 1 to 0.52, or about 1 to 1, specifically reciting all values within these ranges and any ranges created thereby. Where the surface areas of the first coverage area and the second coverage area are too disparate, premature detachment can occur. In FIG. 9C, a moment 999 is shown being applied to the feminine pad. If the ratio of surface area of the first coverage area 981A to the second coverage area 981B for wing 760 is not within the range described previously, the moment 999 can cause premature detachment of the wing 760—particularly in the second coverage area 981B. This problem may be exacerbated where the ratio of surface area of the first coverage area 991A and the second coverage area 991B of wing 770 are also outside of the ranges described previously.

Feminine Pad Construction

Figure 10:
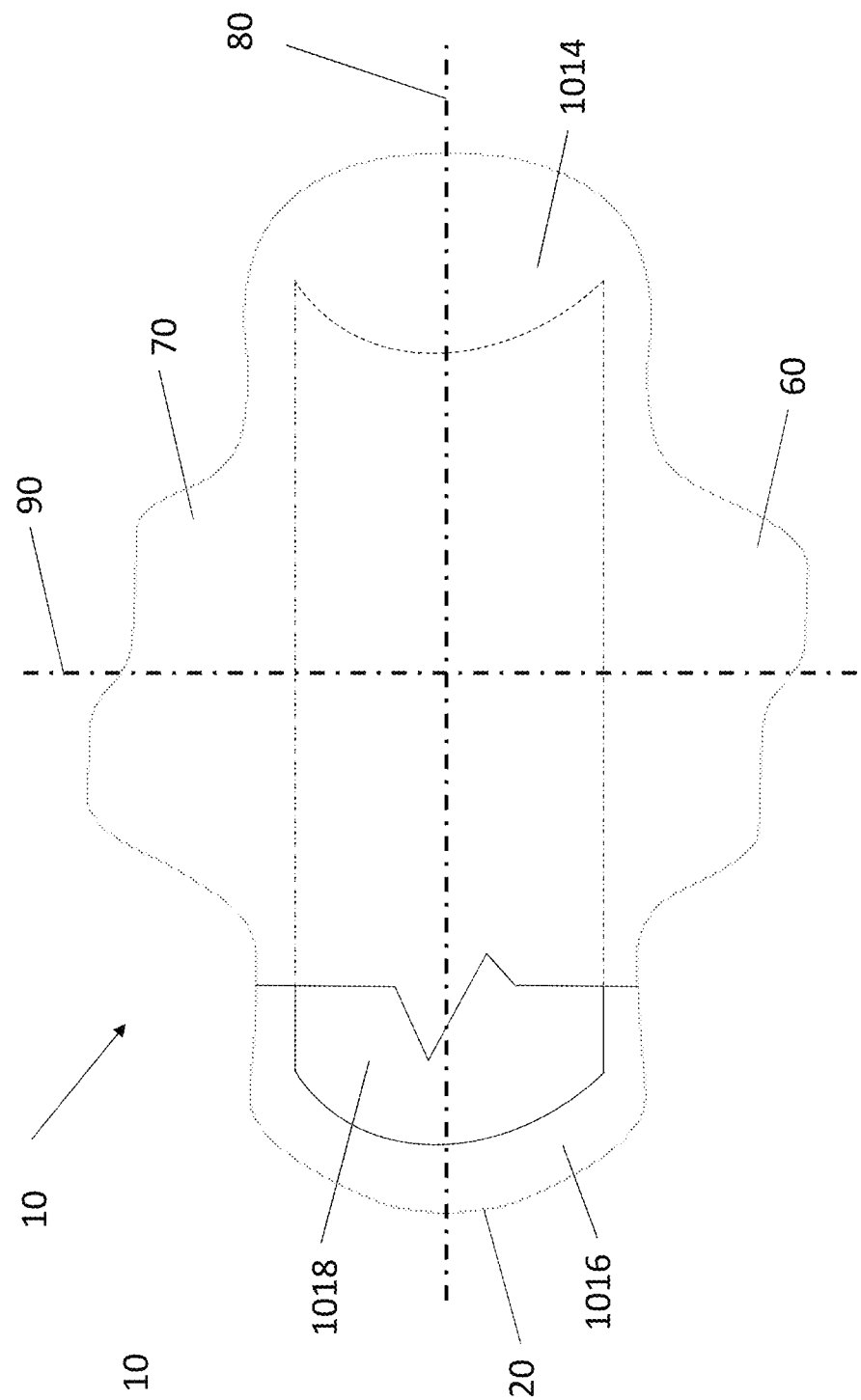
FIG. 10 is a schematic plan view of the feminine pad of FIG. 1A with portions cut-away for ease of view of some of the internal features of the feminine pad.

Referring to FIG. 10, the feminine pad 110 is shown. As noted previously, the feminine pad 10 comprises the chassis 20 and wings extending outboard of the chassis 20. The chassis 20 comprises a liquid permeable topsheet 1014, a liquid impermeable, or substantially liquid impermeable, backsheet 1016, and an absorbent core 1018 positioned intermediate the topsheet 1014 and the backsheet 1016. The wings 60 and 70 may be joined to the topsheet 1014, the backsheet 1016, and/or the absorbent core 1018. The sanitary napkin 1810 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1018 may be any absorbent member which is generally compressible, conformable, non-irritating to the wearer's skin, and capable of absorbing and retaining liquids such as urine, menses, and/or other body exudates. The absorbent core 1018 may be manufactured from a wide variety of liquid-absorbent materials commonly used in disposable absorbent articles such as comminuted wood pulp which is generally referred to as airfelt. The absorbent core 1018 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1018 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1018 may comprise one or more channels, such as two, three, four, five, or six channels.

The absorbent core 1018 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

Other suitable materials for use in absorbent cores comprise open celled foams or pieces thereof. The use of foams in absorbent cores is described in additional detail in U.S. Pat. Nos. 6,410,820; 6,107,356; 6,204,298; 6,207,724; 6,444,716; 8,211,078, and 8,702,668.

In some forms, the absorbent core structure may comprise a heterogeneous mass layer or may utilize methods or parameters such as those described in U.S. patent application Ser. No. 14/715,984, filed May 19, 2015; U.S. patent application Ser. No. 14/750,399, Jun. 25, 2015; U.S. patent application Ser. No. 14/751,969 filed Jun. 26, 2015; U.S. patent application Ser. No. 15/078,132 filed Mar. 23, 2016; U.S. patent application Ser. No. 14/750,596 filed Jun. 25, 2015; U.S. patent application Ser. No. 15/084,902 filed Mar. 30, 2016; U.S. patent application Ser. No. 15/343,989 filed Nov. 4, 2016; U.S. patent application Ser. No. 15/344,273 filed Nov. 4, 2016; U.S. patent application Ser. No. 15/344,294 filed Nov. 4, 2016; U.S. patent application Ser. No. 14/704,110 filed May 5, 2015; U.S. patent application Ser. No. 15/194,894 filed Jun. 28, 2016; U.S. patent application Ser. No. 15/344,050 filed Nov. 4, 2016; U.S. patent application Ser. No. 15/344,117 filed Nov. 4, 2016; U.S. patent application Ser. No. 15/344,177 filed Nov. 4, 2016; U.S. patent application Ser. No. 15/344,198 filed Nov. 4, 2016; U.S. patent application Ser. No. 15/344,221 filed Nov. 4, 2016; U.S. patent application Ser. No. 15/344,239 filed Nov. 4, 2016; U.S. patent application Ser. No. 15/344,255 filed Nov. 4, 2016; U.S. patent application Ser. No. 15/464,733 filed Nov. 4, 2016; U.S. Provisional Patent Application No. 62/437,208 filed Dec. 21, 2016; U.S. Provisional Patent Application No. 62/437,225 filed Dec. 21, 2016; U.S. Provisional Patent Application No. 62/437,241 filed Dec. 21, 2016; or U.S. Provisional Patent Application No. 62/437,259 filed Dec. 21, 2016. The heterogeneous mass layer has a depth, a width, and a height.

In some forms, a combination of absorbent core materials may be utilized. For example, forms are contemplated where a first layer of an absorbent core comprises a foam material or pieces thereof as described previously and a second layer of an absorbent core comprises an airlaid material. Such combinations are described in U.S. Patent Publication No. 2014/0336606 and U.S. Pat. No. 9,649,228.

Figure 14:
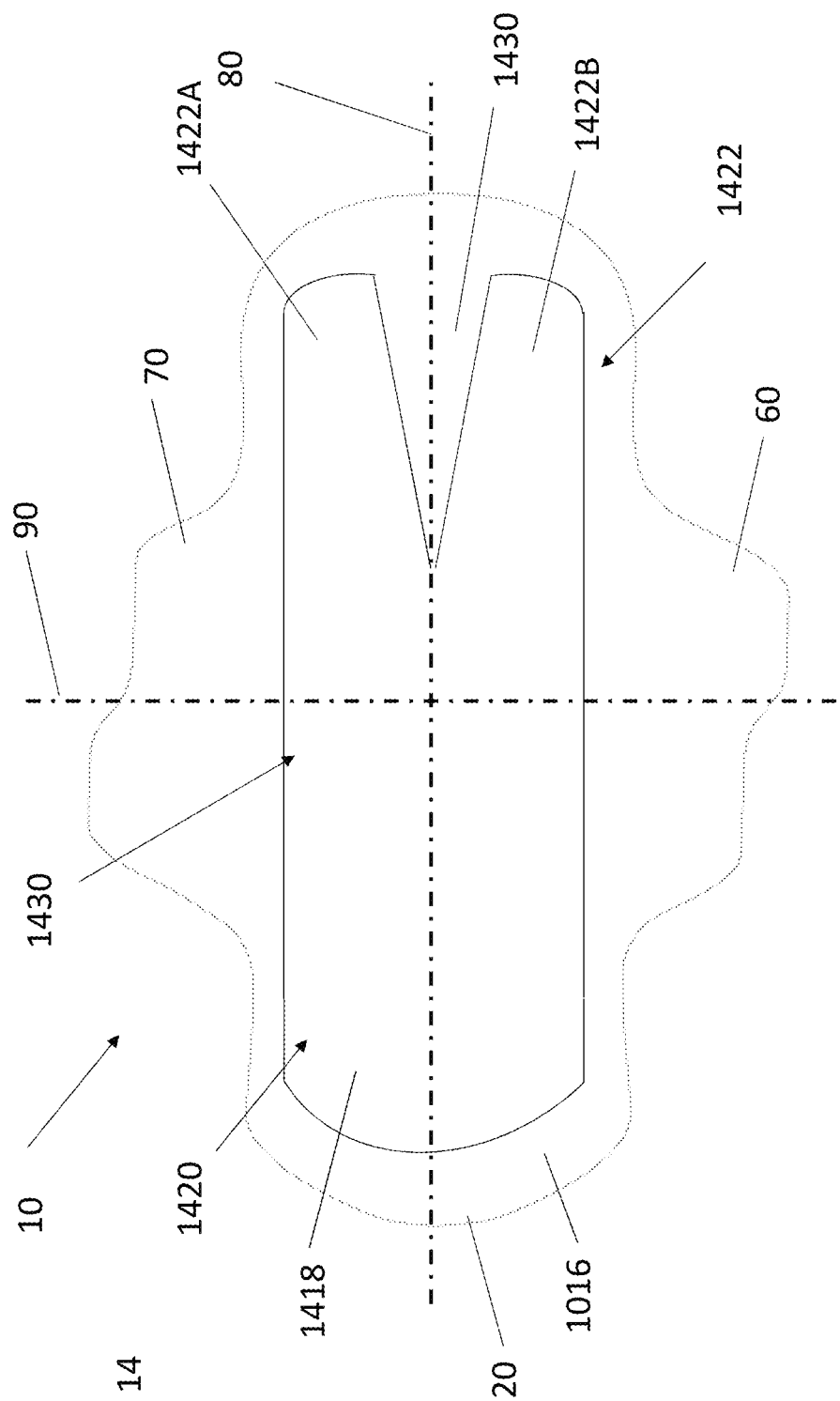
FIG. 14 is a representation showing another feminine pad constructed in accordance with the present disclosure.
Figure 15A:
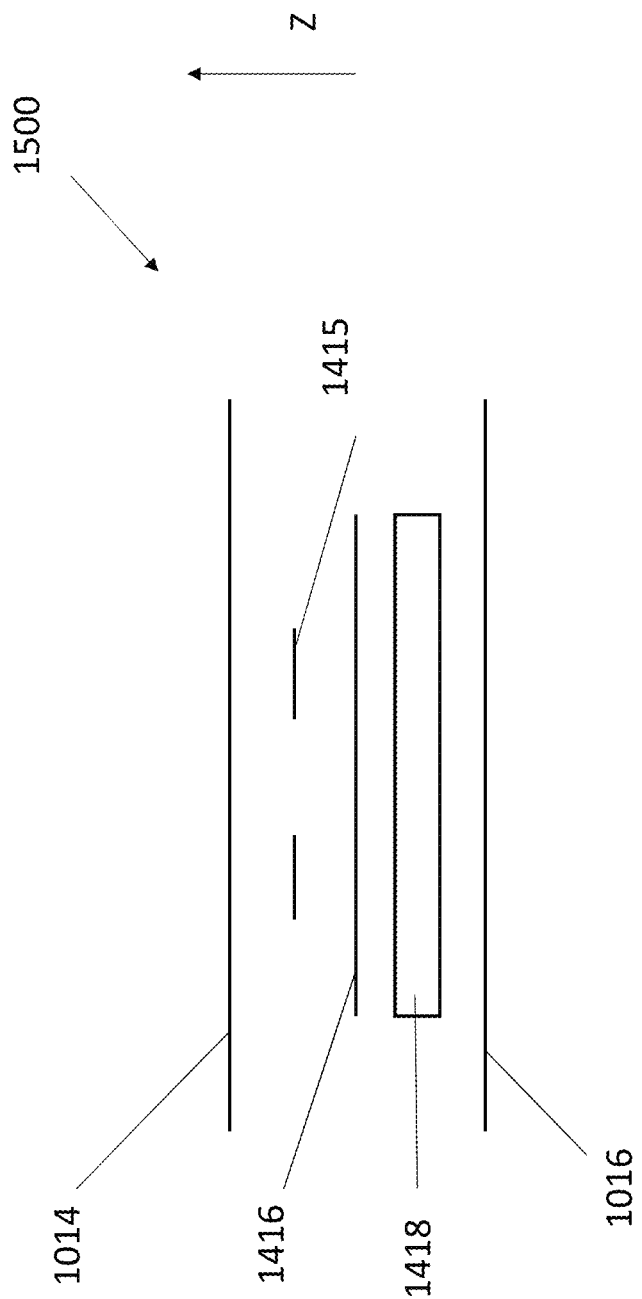
FIG. 15A is a representation showing a cross-section of another feminine pad constructed in accordance with the present disclosure.
Figure 15B:
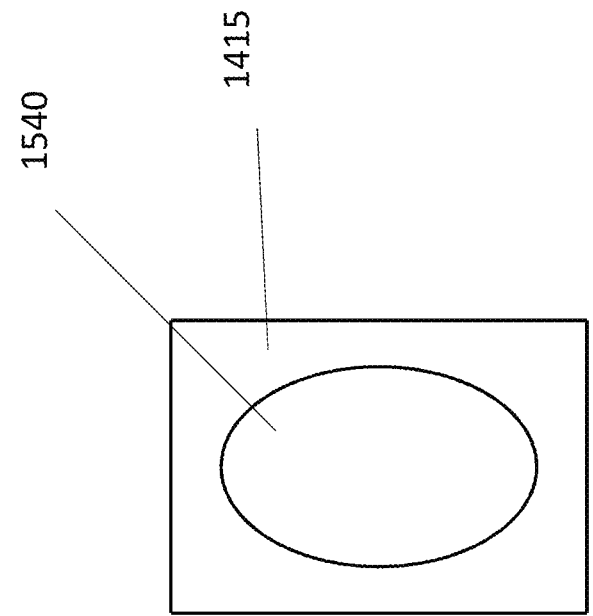
FIG. 15B is a representation showing a supplemental absorbent member of the feminine pad of FIG. 15A.

Additional absorbent core structures are contemplated as shown in FIGS. 14 through 15B. FIG. 14 is a plan view showing the absorbent article 10, excluding a topsheet, such that an absorbent core 1418 constructed in accordance with the present disclosure may be more easily visualized. As shown, the absorbent core 1418 may comprise a first end 1420, a second end 1422 opposite the first end 1420, and an intermediate portion 1430 disposed between the first end 1420 and the second end 1422. The second end 1422 may be associated with that portion of the absorbent article that is positioned adjacent the gluteal groove during use. To facilitate flexibility in that area, a notch 1430 may be provided in the second end 1422 between a first leg 1422A and a second leg 1422B. Because of the notch 1430, the first leg 1422A and the second leg 1422B can move independently of one another. This can allow for increased flexibility in the second end 1422.

Additional forms are contemplated, where the intermediate portion 1430 comprises a width which is less than a width of the first end 1420. In such forms, the intermediate portion 1430 may similarly comprise a width which is less than that of the second end 1422. Additional forms are contemplated where a width of the first end 1420 and/or a width of the intermediate portion 1430 are less than a width of the second end 1422. Conversely, forms are contemplated where a width of the second end 1422 and/or the intermediate portion 1430 are less than a width of the first portion 1420. The variability of the widths of the absorbent core 1418 can build in appropriate flexibility within the absorbent article. For example, for wearer's with a higher body mass index, e.g. BMI>35, flexibility may be needed in the intermediate portion 1430 of the absorbent core 1418 due to the decreased spacing between the thighs of the wearer. For such wearer's, the absorbent core 1420 may be configured such that the width of the intermediate portion 1430 is less than that of the first end 1420 and/or the second end 1430. The identification of the first end 1420, second end 1422, and intermediate portion 1430 is described hereafter. Absorbent cores which comprise a notch 1430 are described in additional detail in U.S. Pat. No. 8,877,999.

Referring now to FIGS. 15A and 15B, an exploded cross-sectional view of an absorbent article 1500 constructed in accordance with the present disclosure is shown. The cross-section shown in FIG. 15A is taken through an opening 1540 (shown in FIG. 15B). The absorbent article 1500 may comprise the backsheet 1016 and topsheet 1014 described herein. Disposed between the topsheet 1014 and backsheet 1016 may be the absorbent core 1418, a secondary topsheet 1416, and a supplemental absorbent member 1415. The secondary topsheet 1416 is discussed in additional detail hereafter. The supplemental absorbent member 1415 is shown in additional detail in FIG. 15B.

As shown, the supplemental absorbent member 1415 may comprise one or more openings 1540, and may be positioned between the secondary topsheet 1416 and the absorbent core 1418. Forms are contemplated where the supplemental absorbent member 1415 may be positioned between the topsheet 1014 and the secondary topsheet 1416. Regardless of its location, the supplemental absorbent member 1415 may be made of a material that is capable of rapidly guiding, transferring and absorbing, in a z-direction, bodily fluid that is delivered to the topsheet 1014 adjacent the supplemental absorbent member 1415.

The supplemental absorbent member 1415 may generally have any shape and/or size desired. Some examples include a shape which resembles a racetrack or a rectangle with semi-circular ends and has a length and/or width less than the overall length and/or width of the backsheet 1016. However, it is to be understood that the first sub-topsheet layer 116 can have a simple rectangular, square, circular, or triangular shape, or a more complex shape having multiple protrusions.

The supplemental absorbent member 1415 can generally have length, width, and thickness dimensions such that it can form a well or cup-like structure that can be used to funnel and hold fluid in a desired location of the absorbent article away from a body-facing surface of the absorbent article. Further, the dimensions of the supplemental absorbent member 1415 can be chosen such that it is wide enough to capture fluid yet still remain comfortable against the wearer's body.

Generally, the length of the supplemental absorbent member 1415 in the longitudinal direction can be from about 20 mm to about 200 mm, from about 40 mm to about 175 mm, or from about 60 mm to about 150 mm, specifically including all values within these ranges and any ranges created thereby. Meanwhile, the width of the supplemental absorbent member 1415 in the transverse direction can be from about 10 mm to about 100 mm, from about 15 mm to about 80 mm, or from about 20 mm to about 60 mm, specifically including all values within these ranges and any ranges created thereby. Additionally, the supplemental absorbent member 1415 can have a thickness ranging from about 100 micrometers (μm) to about 8 mm, from about 500 μm to about 5 mm, or from about 300 μm to about 3 mm, specifically including all values within these ranges and any ranges created thereby.

The supplemental absorbent member 1415 can comprise a variety of materials which can provide varying levels of absorbency. For example, the supplemental absorbent member 1415 can be an additional topsheet layer, a surge layer, a fluid intake layer, or an absorbent core layer. Any materials known in the art can be used in the supplemental absorbent member 1415, such as the topsheet layer materials discussed herein, and the absorbent core and secondary topsheet materials discussed herein. Further, the supplemental absorbent member 1415 can be synthetic, cellulosic, or a combination of synthetic and cellulosic materials. In one particular example, multifunctional airlaid material such as airlaid cellulosic tissues may be suitable for use in the supplemental absorbent member 1415. The airlaid cellulosic tissue may have a basis weight ranging from about 10 gsm to about 300 gsm, or between about 40 gsm to about 150 gsm, specifically including all values within these ranges and any ranges created thereby. The airlaid tissue may be formed from hardwood and/or softwood fibers. The airlaid tissue has a fine pore structure and can provide an excellent wicking capacity, especially for menses.

The opening 1540 may be of any suitable shape. Some examples include oval, circular, rectangular, square, triangular, or the like. The supplement absorbent member 1415 can serve to funnel liquid insults to the absorbent core from the topsheet of the absorbent article. The opening 1540 can also form a cup or well like structure for holding fluid and preventing its leakage away from a central region of the absorbent article and towards the edges.

Generally, the opening 1540 can have a length in a longitudinal direction that is from about 15 mm to about 150 mm, from about 20 mm to 100 mm, or from about 30 mm to about 75 mm, specifically reciting all values within these ranges and any ranges created thereby. The opening 1540 can have a width in the transverse direction that is from about 10 mm to about 80 mm, from about 15 mm to about 60 mm, or from about 20 mm to about 40 mm, specifically reciting all values within these ranges and any ranges created thereby. The size of the opening 1540 can allow the supplemental absorbent member 1415 to sufficiently bend to conform to the wearer's body, which can prevent leakage of bodily fluids due to channels that could be created in the absorbent article upon the introduction of compressive forces. It is also desirable that the opening 1540 be large enough for a consumer to easily view and place it directly under a vaginal opening so that it is located underneath the portion of the body-facing surface of the absorbent article having primary contact with bodily fluids.

In this regard, the proper placement of the absorbent article can be further facilitated where the supplemental absorbent member 1415 comprises a visual contrast, e.g. a delta E of greater than 2.0 on the CIELab color space, when compared to its surround material of the absorbent article. CIElab color space is well known in the art as are measurements for ascertaining visual contrast between two surfaces. The visual contrast may be provided in a variety of ways. For example, the supplemental absorbent member 1415 may be dyed, printed, or otherwise colored such that it is distinctly in contrast with other layers of the absorbent article or at least distinctly in contrast with portions of the absorbent article which are directly adjacent to the supplement absorbent member 1415. Supplemental absorbent members, topsheets, and other absorbent article layer arrangements are discussed in additional detail in U.S. Patent Application Publication No. 2015/0313766 and U.S. Pat. No. 9,237,975.

The feminine pad 1010 may comprise additional layers between the topsheet 1014 and the absorbent core 1018. For example, the feminine pad 1010 may comprise a secondary topsheet and/or an acquisition layer positioned between the topsheet 1014 and the absorbent core 1018. One suitable example of a secondary topsheet is with regard to a spunlace nonwoven. Suitable spunlace nonwovens are discussed in additional detail in U.S. Patent Publication No. 2015/0351976. In some forms, the secondary topsheet may comprise superabsorbent similar to the superabsorbent in the absorbent core or different than the absorbent core.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 $g/m^2$ to about 35 $g/m^2$. However, it should be noted that other flexible liquid impervious materials may be used as the backsheet. Herein, "flexible" refers to materials which are compliant and which will readily conform to the general shape and contours of the wearer's body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

The topsheet 1014 is positioned adjacent a body-facing surface of the feminine pad 1010. The topsheet 1014 may be joined to the backsheet 1016 by attachment methods (not shown) such as those well known in the art. The topsheet 1014 and the backsheet 1016 may be joined directly to each other in the feminine pad periphery and may be indirectly joined together by directly joining them to the absorbent core 1018 by any suitable attachment method.

The topsheet 1014 may be compliant, soft feeling, and non-irritating to the wearer's skin. Further, the topsheet 1014 may be liquid pervious permitting liquids (e.g., urine, menses) to readily penetrate through its thickness. Some suitable examples of topsheet materials include films, nonwovens, laminate structures including film/nonwoven layers, film/film layers, and nonwoven/nonwoven layers. Other exemplary topsheet materials and designs are disclosed in U.S. Patent Application Publication Nos. 2016/0129661, 2016/0167334, and 2016/0278986.

Figure 11:
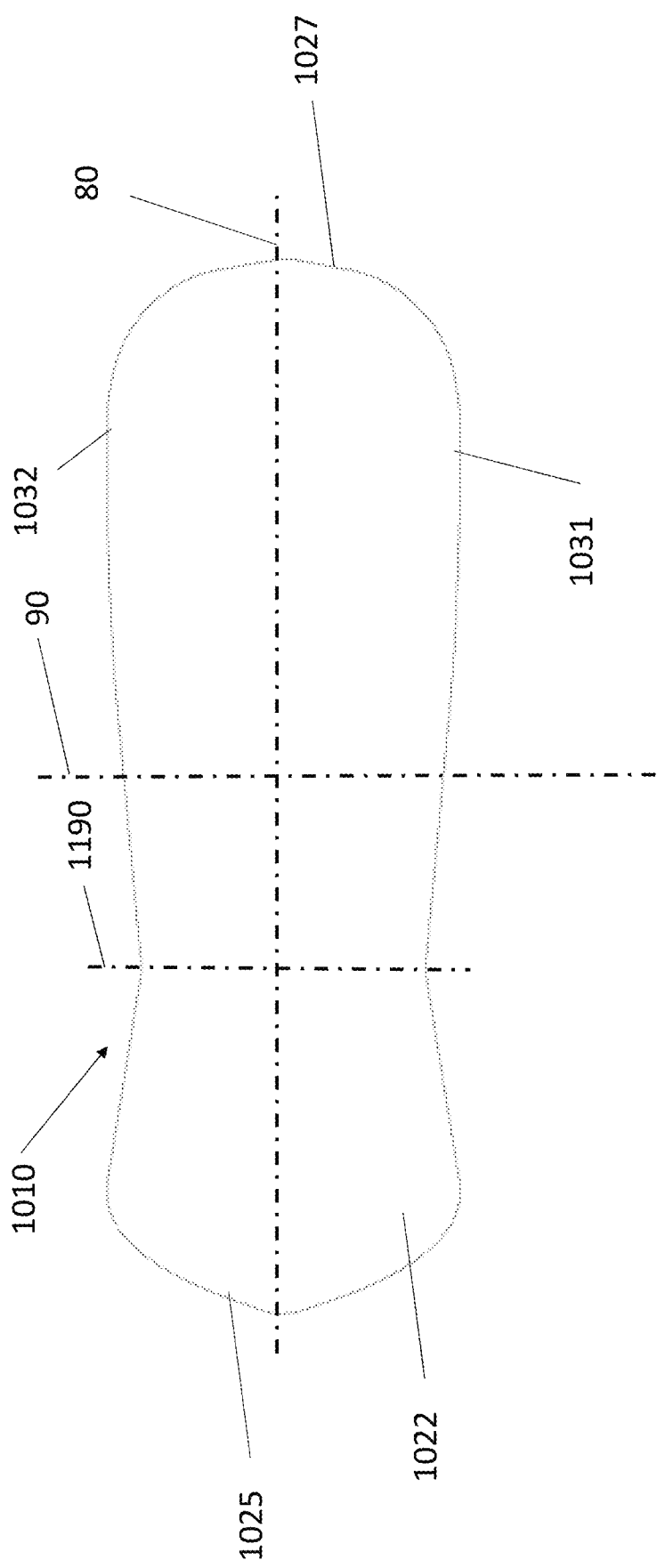
FIG. 11 is a schematic plan view of a secondary topsheet suitable for use with the feminine pads of the present disclosure.

As noted previously, the feminine pad 1010 may comprise a secondary topsheet 1022 or an acquisition layer disposed between the topsheet 1014 and the absorbent core 1018 as shown in FIG. 11. The secondary topsheet 1022 may comprise a first end 1025 and an opposing second end 1027 and a pair of longitudinally opposing side edges 1031 and 1032 connecting the first end 1025 and the second end 1027. As shown, the secondary topsheet 1022 may be asymmetrical about the lateral centreline 90.

The secondary topsheet 1022 may additionally comprise a variable width. For example adjacent the first end 1025, the secondary topsheet may have a first width. The width may decrease toward a flex axis 1190. The flex axis 1190 may comprise the smallest width of the secondary topsheet 1022 and may be disposed on a first side of the lateral centreline 90.

The flex axis 1190 can provide the feminine pad with reduced stiffness in the area of the pad adjacent the flex axis 1190. Because the absorbent core and secondary topsheet are typically the thickest materials in the feminine pad, they can also be the stiffest. So, the creation of a flex axis 1190 can provide the feminine pad with the ability to conform to the body of the wearer in the area of the flex axis 1190. And conformance of the feminine pads of the present disclosure to a user's body can provide for a more comfortable use experience for the user.

The wings of the feminine hygiene pads of the present disclosure may be integrally formed as part of the topsheet. In some forms, the wings may be integrally formed as part of the backsheet. In some forms, the wings may be integrally formed as part of the topsheet and the backsheet. In some forms, the wings may be integrally formed with additional layers—described herein—of the feminine hygiene pad. Yet in other forms, the wings may be formed discretely and joined to the chassis.

EXAMPLES

Figure 12:
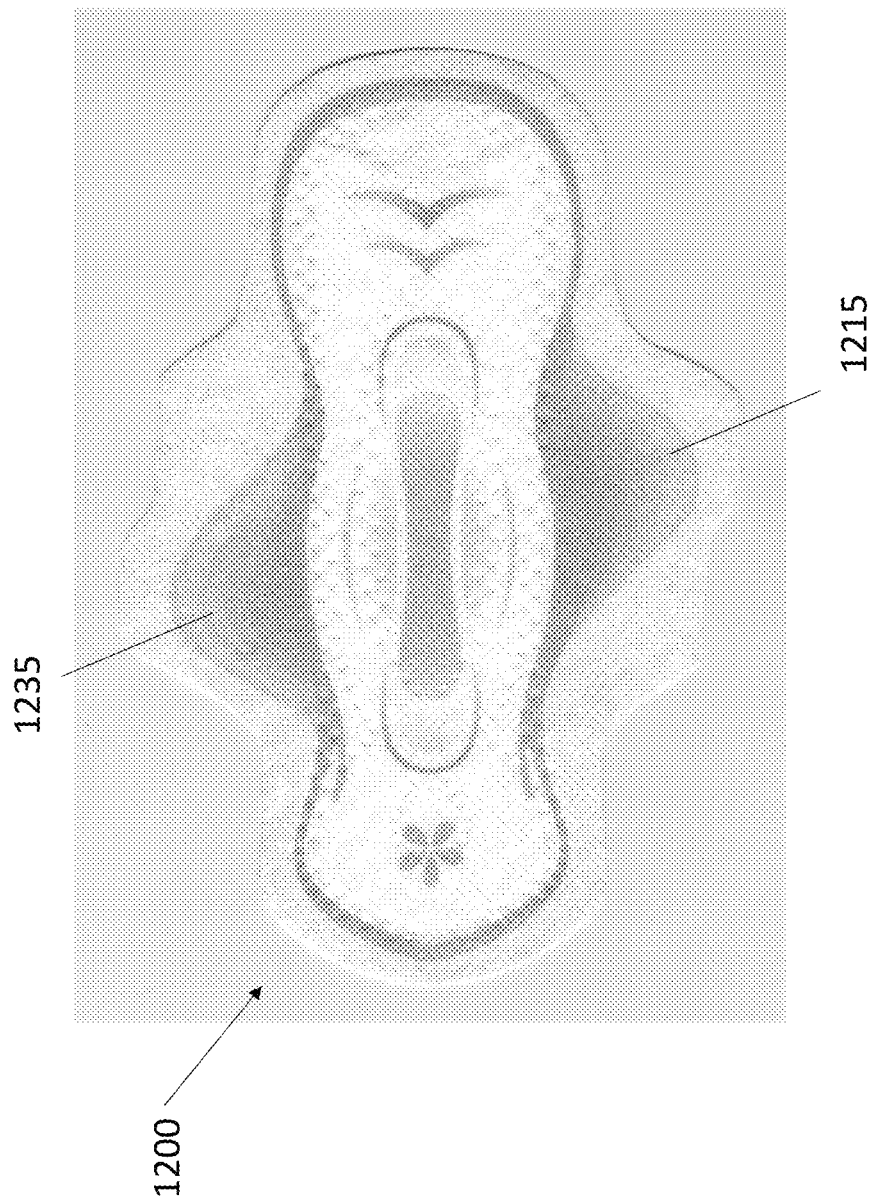
FIG. 12 is a photograph showing a feminine pad in accordance with the present disclosure.
Figure 13:
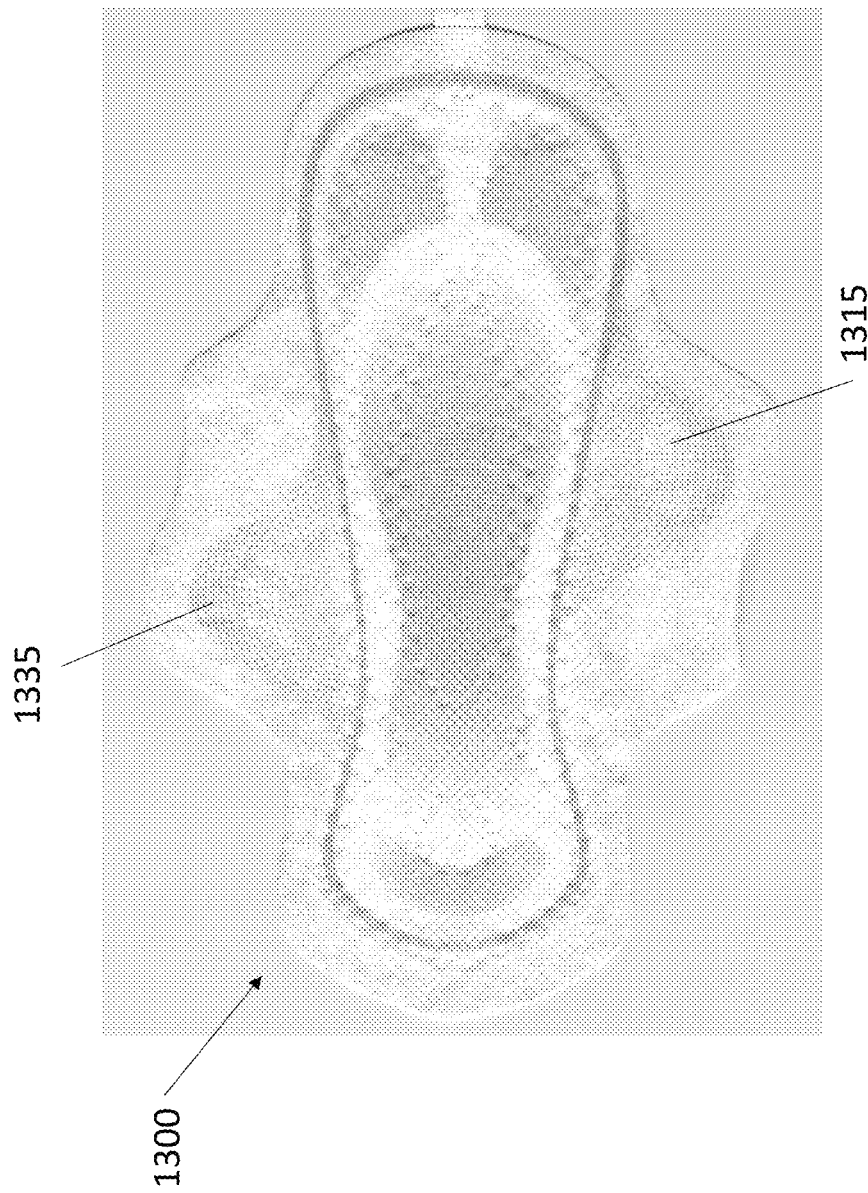
FIG. 13 is a photograph showing another feminine pad in accordance with the present disclosure.

Examples of feminine pads constructed in accordance with the present disclosure are provided with regard to FIGS. 12 and 13. In FIG. 12, a feminine pad 1200 is shown comprising a first visual signal 1215 and a second visual signal 1235. In FIG. 13, a feminine pad 1300 is shown comprise a first visual signal 1315 and a second visual signal 1335. Various measurements were taken in accordance with the descriptions in the specification. The various measurements are provided below in Tables 1 and 2. For the sake of clarity, the samples identified as 1200 (1) are associated with a first wing of the pad 1200 in FIG. 12, and 1200 (2) are associated with the second wing of the pad 1200 in FIG. 12. Similarly, for pad 1300, the measurements are labeled 1300 (1) for the first wing of the pad 1300 in FIGS. 13 and 1300 (2) for the second wing of the pad 1300 in FIG. 13.

TABLE 1

| Pad | Wf (mm) | Ws (mm) | Wing Length (mm) | Distal Zone Area (mm$^2$) | Proximal Zone Area (mm$^2$) |
|---|---|---|---|---|---|
| 1200 (1) | 85.6 | 87.4 | 115.8 | 1374.2 | 1122.6 |
| 1200 (2) | | | 116.8 | 1341.9 | 1025.8 |
| 1300 (1) | 85.7 | 87.6 | 120.8 | 1361.0 | 1239.4 |
| 1300 (2) | | | 122.3 | 1449.3 | 1125.5 |

TABLE 2

| Pad | Visual Signal Area - Distal (mm$^2$) | Visual Signal Area - Proximal (mm$^2$) |
|---|---|---|
| 1200 (1) | 677.4 | 57.4 |
| 1200 (2) | 587.7 | 216.1 |
| 1300 (1) | 676.2 | 113.0 |
| 1300 (2) | 677.4 | 18.3 |

In order to safeguard the experiential aspect of the pads of the present disclosure, packaging of the absorbent pads 10 described herein should be carefully reviewed. In general, absorbent pads are packaged in a bi-folded or tri-folded state. However, care should be taken to ensure that the wings of the pad 10 are not caught in the folds. In such instances, a fold line which crosses the wings may increase the difficulty in application of the pad to underwear due to the folded wings. For the pads of the present disclosure, a first fold line 1618 may be disposed at a distance Lf1 from a first end of the pad 10. In some forms, the distance Lf1 may be from about 50 mm to about 110 mm, or from about 60 to about 100 mm, specifically including all values within these ranges and any ranges created thereby. As noted herein, forms are contemplated where pitch length PL increases across an array of pads. Similar to the increase in pitch length PL, the length Lf1 may increase across an array. For example, for a first plurality of pads, a length Lf1 may be greater than about 50 mm, greater than about 60 mm, greater than about 70 mm, less than about 80 mm, specifically including all values within these ranges and any ranges created thereby. For a second plurality of pads, the length Lf1 may be greater than 70 mm, greater than 80 mm, greater than 90 mm, greater than 100 mm, or less than 110 mm, specifically including all values within these ranges and any ranges created thereby. Forms are contemplated where a third plurality of absorbent articles has a first fold line which has the length Lf1 of between 60 mm and 100 mm or between 70 mm and 90 mm, specifically including all values within these ranges and any ranges created thereby.

A ratio of the length Lf1 to the pitch length PL can be between about 0.2 to about 0.4, between about 0.25 to 0.35, or between about 0.28 to about 0.3, specifically including all values within these ranges and any ranges created thereby. A ratio of lengths Lf1 to Lf2 can be from about 0.3 to about 0.5, from about 0.35 to about 0.45, or about 0.4 to 0.44.

Similarly, a second fold line 1620 may be positioned having a length Lf2 from the first end which is between about 130 mm to about 250 mm, between 140 mm to about 240 mm, between 150 mm to about 230 mm, specifically including all values within these ranges and any ranges created thereby. Where an array of pads is provided, the length Lf2 can vary as described herein regarding the length Lf1. For example, for a first plurality of pads, the length Lf2 can be between about 130 mm to about 170 mm, from about 140 mm to about 160 mm, or from between 150 mm to about 156 mm, specifically including all values within these ranges and any ranges created thereby. For a second plurality of pads within the array, the length Lf2 may be between 170 mm to about 200 mm, between about 180 mm to 190 mm, specifically including all values within these ranges and any ranges created thereby. For a third plurality of articles, the length Lf2 may be between 180 mm and 210 mm, between 190 mm and 205 mm, or between 195 mm and 201 mm, specifically including all values within these ranges and any ranges created thereby. For a fourth plurality of pads, the length Lf2 may be between about 200 mm and 240 mm, between about 210 mm and 230 mm, or between about 220 mm and 225 mm, specifically including all values within these ranges and any ranges created thereby.

Test Methods

Visual Signal Area Measurement Method

The intent of the Visual Signal Area measurement is to determine the amount of printed color and/or emboss area within a respective zone of an absorbent article wing. The printed color area and emboss area measurements are obtained from article images acquired using a flatbed scanner. The scanner is capable of scanning in reflectance mode at a resolution of 500 dpi and 24 bit color (a suitable scanner is an Epson Perfection V750 Pro from Epson America Inc., Long Beach Calif. or equivalent). The scanner is interfaced with a computer running an image analysis program (a suitable program is ImageJ v. 1.50 or equivalent, National Institute of Health, USA). The article images are distance calibrated against an acquired image of a ruler certified by NIST. The resulting image is then analyzed using the image analysis program to identify the boundaries of the printed color and emboss regions and calculate the Visual Signal Area.

The ruler is placed on the center of the scanner bed, oriented parallel to the sides of the scanner glass, and the scanner lid is closed. A calibration image of the ruler is acquired in reflectance mode at a resolution of 500 dpi (approximately 19.7 pixels per mm) and 24 bit color. The calibration image is saved as an uncompressed TIFF format file. The scanner lid is opened and the ruler removed. After obtaining the calibration image, all articles are scanned under the same conditions and measured based on the same calibration file. Next, the article is placed onto the center of the scanner bed, lying flat, with the color printed surface of the article facing the scanner's glass surface. The article is covered with a white background (in this test method white is defined as having $L^*>94$, $-2<a^*<2$, and $-2<b^*<2$) and the scanner lid is closed. A scanned image of the article is acquired and saved as an uncompressed TIFF format file. If the size of the article exceeds the available scanning area, multiple scans are obtained covering the entire article and stitched together into a single image for analysis. A total of five substantially similar replicate articles are scanned in like fashion.

The calibration image file is opened in the image analysis program and a linear distance calibration is performed using the imaged ruler. This distance calibration scale is applied to all subsequent article images prior to analysis. An article image is opened in the image analysis program and the distance scale is set. Using the image analysis program, the boundaries of the respective zones of the article wing, within which the printed color area is to be measured, is identified and defined as described within the specification. Using the image analysis program, the boundaries of any printed color regions within the respective zones are identified and defined. Identification of color region boundaries is performed with the intent of defining them as they would be discerned by a human viewer under standard lighting conditions with the unaided eye if being viewed face on in a flat configuration at approximately an arm's length distance. In like fashion, the boundaries of any emboss regions within the respective zones are identified and defined. The area of each of the individual printed color and emboss regions are calculated within the respective zones to the nearest 0.1 $mm^2$. Any area containing both printed color and emboss regions is only calculated once. The total area of printed color and emboss regions is calculated by summing up the areas of the individual printed color and emboss regions. This value is recorded as the Visual Signal Area to the nearest 0.1 $mm^2$. In like fashion, the remaining four specimen images are analyzed. The average Visual Signal Area is calculated and reported to the nearest 0.1 $mm^2$ for the five replicates.

Intermediate Portion Test Method

The Intermediate Portion Test Method is used to determine the intermediate portion length index value.

A two-dimensional shape, defined by the projection of a planar core perpendicular to both its longitudinal and transverse axes, is captured and is hereafter referred to as the core projection. The core projection retains the same longitudinal and transverse axes of the core itself. The centroid of the core projection is calculated, and the position of the centroid along the longitudinal axis of the core projection is defined as the core centroid point. A line extending through the core centroid point and parallel to the transverse axis is used to partition the core projection into two sub-shapes, a first core projection and a second core projection. The centroids of the first core projection and second core projection are calculated and defined as the first centroid and second centroid, respectively. The position of the first centroid along the longitudinal axis of the core projection is defined as the first core centroid point. The position of the second centroid along the longitudinal axis of the core projection is defined as the second core centroid point.

Lines extending through the first and second centroid points parallel to the transverse centerline 90 of the core projection delineate the boundaries between the first end, second end, and intermediate portion. The length of the intermediate portion along the longitudinal axis is calculated and reported to the nearest 0.1 mm.

The intermediate portion length index value is calculated by dividing the length of the intermediate portion by the total length of the core projection along the longitudinal axis and is a dimensionless ratio reported to the nearest 0.01.

All measures are performed on five substantially similar absorbent cores and reported as the arithmetic mean of the five values.

Linear Distances

Linear distances may be measured by any appropriate instrument that is calibrated and capable of a measurement to the nearest 0.1 mm. Area measurements are made using the projected area of the article, as viewed orthogonally to the plane of the article length and width, in square millimeters to the nearest 0.1 $mm^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular forms of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A feminine hygiene article having a chassis comprising a topsheet, a backsheet, and an absorbent core disposed between the topsheet and the backsheet, a longitudinal centerline and a lateral centerline perpendicular to the longitudinal centerline, a first end, an opposing second end, and an intermediate region connecting the first end and the second end, the first end having a width Wf and the second end having a width Ws; the feminine hygiene article further comprising:
    a first wing extending laterally outboard of the chassis having a first leading edge extending outboard of the chassis, a first trailing edge extending outboard of the chassis and one or more edges connecting the first leading edge and the first trailing edge, wherein the first wing has a first length and a first bisecting line bisecting the first length, the first bisecting line forming, at least a portion, of a boundary between a first distal zone and a first proximal zone, wherein the first distal zone is disposed more outboard of the chassis than the first proximal zone, and wherein the first proximal zone forms the uppermost portion of the first wing, wherein the first wing is asymmetric about the first bisecting line, wherein the first wing further comprises a first surface and an opposing second surface, a first adhesive area and a second adhesive area disposed on the second surface, wherein the first adhesive area is disposed asymmetrically with respect to the first bisecting line;
    a second wing extending laterally outboard of the chassis having a second leading edge extending outboard of the chassis, a second trailing edge extending outboard of the chassis and one or more edges connecting the second leading edge and the second trailing edge, wherein the second wing has a second length and a second bisecting line bisecting the second length, and the second bisecting line forming, at least a portion, of a second distal zone and a second proximal zone, wherein the second distal zone is disposed more outboard of the chassis than the second proximal zone, and wherein the second proximal zone forms the lowermost portion of the second wing, wherein the second wing further comprises a first surface and an opposing second surface, a third adhesive area and a fourth adhesive area disposed on the second surface, wherein the third adhesive area is disposed asymmetrically with respect to the second bisecting line;
    a first visual signal disposed on the first wing, wherein the first visual signal comprises a first visual signal area, and wherein the first visual signal area is disposed asymmetrically with respect to the first bisecting line as determined by the Visual Signal Area Measurement Method disclosed herein; and
    a second visual signal disposed on the second wing, wherein the second visual signal comprises a second visual signal area, and wherein the second visual signal area is disposed asymmetrically with respect to the second bisecting line as determined by the Visual Signal Area Measurement Method disclosed herein.

2. The feminine hygiene article of claim 1, wherein a ratio of the first end width (Wf) to the second end width (Ws) is from about 0.47 to about 1.3.

3. The feminine hygiene article of claim 1, wherein a larger portion of the first visual signal area is disposed in the first distal zone than in the first proximal zone in accordance with the Visual Signal Area Measurement Method method disclosed herein and wherein a larger portion of the second visual signal area is disposed in the second distal zone than in the second proximal zone in accordance with the Visual Signal Area Measurement Method disclosed herein.

4. The feminine hygiene article of claim 3, wherein the first distal zone is more proximal to the second end than the first proximal zone and wherein the second distal zone is more proximal to the first end than the second proximal zone.

5. The feminine hygiene article of claim 4, wherein the first distal zone is more proximal to the second end than the second distal zone.

6. The feminine hygiene article of claim 5, wherein the first distal zone and the second distal zone are longitudinally offset from one another.

7. The feminine hygiene article of claim 3, wherein the first distal zone is disposed on a second side of the lateral centerline of the feminine hygiene article, and the second distal zone is disposed on a first side of the lateral centerline.

8. The feminine hygiene article of claim 3, wherein a first distal edge connects the first leading edge and the first trailing edge and wherein a second distal edge connects the second leading edge and the second trailing edge.

9. The feminine hygiene article of claim 3, wherein a first proximal edge extends from the first leading edge toward the first trailing edge, wherein a first distal edge extends from the first trailing edge towards the first leading edge, and wherein a first transition edge connects the first proximal edge and the first distal edge.

10. The feminine hygiene article of claim 9, wherein a second proximal edge extends from the second trailing edge towards the second leading edge, wherein a second distal edge extends from the second leading edge toward the second trailing edge, and wherein a second transition edge connects the second proximal edge and the second distal edge.

11. The feminine hygiene article of claim 1, wherein the first end comprises longitudinal side edges, and wherein the longitudinal side edges are inclined with respect to the longitudinal centerline such that the first end width (Wf) decreases to about 53 percent of (Wf).

12. The feminine hygiene article of claim 11, wherein the second end comprises longitudinal side edges, and wherein the longitudinal side edges are inclined with respect to the longitudinal centerline such that the second end width (Ws) decreases to about 65 percent of (Ws).

13. The feminine hygiene article of claim 1, wherein the first bisecting line and the second bisecting line are disposed on a first side of the lateral centerline more proximal to the first end.

14. The feminine hygiene article of claim 1, wherein the first bisecting line and the second bisecting line are disposed on a second side of the lateral centerline more proximal to the second end.

15. The feminine hygiene article of claim 1, wherein the first bisecting line and the second bisecting line are co-linearly disposed with the lateral centerline.

16. The feminine hygiene article of claim 1, wherein the first wing further comprises a grasping area, a first coverage area, and a second coverage area, wherein the first coverage area and the second coverage area have a ratio of about 1 to 1.48.

17. The feminine hygiene article of claim 16, wherein the second wing further comprises a grasping area, a first coverage area, and a second coverage area, wherein the first coverage area and the second coverage area have a ratio of 1 to 1.48.

18. The feminine hygiene article of claim 3, wherein the first distal zone has a distal zone adhesive length and wherein the first adhesive area has an adhesive area length, and wherein a ratio of the distal zone adhesive length to the adhesive area length is from about 1.15 to about 4.6.

19. The feminine hygiene article of claim 1, wherein a ratio of the first end width (Wf) to the second end width (Ws) is from about 0.75 to about 1.1.

20. The feminine hygiene article of claim 1, wherein the first wing further comprises a grasping area, a first coverage area, and a second coverage area, wherein the first coverage area and the second coverage area have a ratio of about 1 to 0.52.

* * * * *